US007674876B2

(12) United States Patent
Dreyer et al.

(10) Patent No.: US 7,674,876 B2
(45) Date of Patent: Mar. 9, 2010

(54) SYNTHESIS OF NOVEL MONOMERS CONTAINING THE TRIFLUOROVINYLIDENE GROUP AND THE CYANATO GROUP AND POLYMERS THEREOF

(75) Inventors: Christian Dreyer, Niederwörresbach (DE); Monika Bauer, Senzig (DE); Suresh S. Iyer, Clemson, SC (US); Dennis W. Smith, Seneca, SC (US)

(73) Assignees: Fraunhofer-Gesellschaft zur Förderung der angewandten Forschung e.V., München (DE); Clemson University, Clemson, SC (US)

( * ) Notice: Subject to any disclaimer, the term of this patent is extended or adjusted under 35 U.S.C. 154(b) by 476 days.

(21) Appl. No.: 11/420,069

(22) Filed: May 24, 2006

(65) Prior Publication Data

US 2006/0293502 A1 Dec. 28, 2006

Related U.S. Application Data

(60) Provisional application No. 60/594,990, filed on May 25, 2005.

(51) Int. Cl.
*C08G 73/00* (2006.01)
*C07C 255/03* (2006.01)
*C07C 261/04* (2006.01)

(52) U.S. Cl. ........................ 528/422; 558/389; 560/301

(58) Field of Classification Search ................. 558/389; 528/422; 560/301
See application file for complete search history.

(56) References Cited

OTHER PUBLICATIONS

Perpall et al., Fluoropolymer Functionalization of Structured carbon Particles; Polymer Preprints (American Chemical Society Division of Polymer Chemistry), 2005, 46(2); pp. 605-606.*

* cited by examiner

*Primary Examiner*—James O Wilson
*Assistant Examiner*—Ebenezer Sackey
(74) *Attorney, Agent, or Firm*—Gudrun E. Huckett

(57) ABSTRACT

Novel hybrid monomers containing both the aryltrifluorovyinyloxyether-group (TFVE-group) and the cyanato-group, their synthesis, and the synthesis of polymers made from these new hybrid monomers are disclosed.

20 Claims, 11 Drawing Sheets

SYNTHESIS OF NOVEL MONOMERS CONTAINING THE TRIFLUOROVINYLIDENE GROUP AND THE CYANATO GROUP AND POLYMERS THEREOF

This application claims the benefit of U.S. provisional application Ser. No. 60/594,990 having a filing date of May 25, 2005. The entire disclosure of said provisional application Ser. No. 60/594,990 is herewith incorporated by reference.

FIELD OF THE INVENTION

The present invention relates to novel hybrid monomers containing both the aryltrifluorovinyloxyether-group (TFVE-group) (A) and the cyanato-group (B), polymers derived from these new hybrid monomers, and the synthesis of said hybrid monomers and said polymers.

(A)

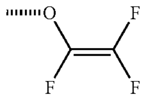

(B)

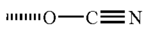

Also covered are copolymers consisting of or comprising one or more of the novel hybrid-monomers and at least one aryltrifluorovinyloxyether-group containing monomer and/or at least one cyanato-group containing monomer, as well as the synthesis of said copolymers. Also covered are (co)polymers containing triazine rings, wherein the said triazine rings are derived from cyclotrimerization of the said cyanato groups, (co)polymers containing perfluorocyclobutane group, wherein the perfluorocyclobutane groups are derived from 2+2 cycloaddition of the TFVE-groups, containing optionally also free cyanato groups, and (co)polymers containing both, triazine rings (obtained via cyclotrimerization of cyanate groups) and perfluorocyclobutane groups (obtained via 2+2 cycloaddition of TFVE groups). Such novel (co) polymers having a variety of different compositions have outstanding properties and can therefore advantageously be used in different areas (e.g. as waveguide materials, integrated optical devices such as arrayed waveguide gratings (AWGs), thermo-optical switches, electro-optic modulators, and light emitting materials, optical fibers, optical coatings, adhesives and encapsulants for μ-electronics and as low-k-materials).

BACKGROUND OF THE INVENTION

Today, in a lot of areas of high technology (integrated optics, μ-electronics, nanotechnology, aeronautics, (outer) space, automotive etc.) there are significant demands on new (polymeric) materials with outstanding and new properties. In order to satisfy such demands, a variety of high-performance polymers have been developed. Under these are polycyanurate ester resins and perfluorocyclobutyl (PFCB) polymers.

Polycyanurate ester resins are a lesser known class of high-performance-polymers, developed in the late 1960s as a base material for printed circuit boards. They show a number of outstanding properties, for example high thermal stability ($T_g$ typically around 250-400° C.), low optical loss, low birefringence, low dielectric constant, good adhesion properties on different substrates, excellent resistance against most common solvents and amazing mechanical properties. They are used as encapsulants and adhesives, as underfiller in microelectronics, as low-k materials, in flame stable composites, in laminates, as friction materials, in lightweight construction, in automotive engineering, in the aircraft industry, and for outer space applications. The resins are prepared from cyanate monomers $$N{\equiv}C—O—R—O—C{\equiv}N$$

where residue R can be e.g. a fluorinated or semifluorinated (partly fluorinated) aliphatic chain, a residue comprising or consisting of one or more than one aromatic rings, the ring(s) directly linked to each other through a C—C bond or linked to each other via —O—, —S—, —$CR^{17}R^{18}$—, —$SO_2$—, wherein $R^{17}$, $R^{18}$ are an optionally substituted alkyl group or aryl group. Alternatively, R can also be selected from the group comprising napthalene, anthracene or higher homologues. Residue R can also contain additional (third, fourth etc.) cyanato-groups.

The monomers are typically obtained by reacting respective, —OH containing compounds with halogencyanide under alkaline (basic) conditions as reported by Bauer and Martin (MARTIN, D.; BAUER, M.: cyanic Acid Esters from Phenols: Phenyl cyanate. In: Organic Synthesis 61 (1981), pp. 35-38). The said monomers undergo polycyclotrimerization to generate polycyanurates as shown below. In this trimerization reaction, an (at least) difunctional cyanate molecule will react with two other cyanate molecules to form a triazine ring. In case of using difunctional cyanates, i.e. compounds carrying two OCN groups, this triazine will comprise three free reactive —OCN groups and, under respective conditions, will react with further monomers to form pentamer, heptamer or higher oligomers, until a highly branched three dimensional network is built up. At sufficiently high temperatures and appropriate reaction times an almost complete transformation of the cyanato-groups can be achieved. No byproducts are found for this reaction. (see scheme (I) below):

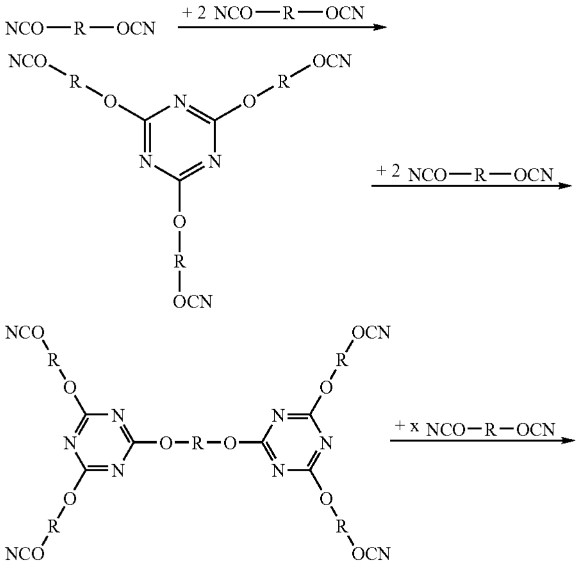

-continued

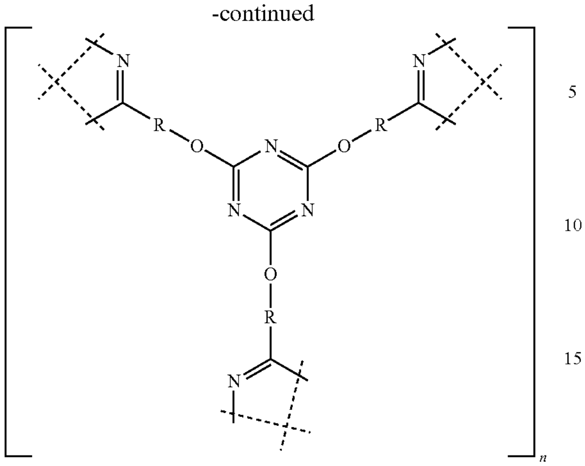

Such polycyanurates show a number of outstanding properties, like high thermal stability, low optical loss, low dielectric constant, good adhesion properties on different surfaces and high mechanical strength. This makes these reactive resins suitable for a lot of applications.

Perfluorocyclobutane-polymers can be obtained from at least difunctional TFVE-containing-monomers:

(Ia)

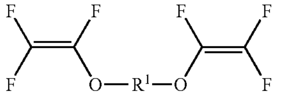

(Ib)

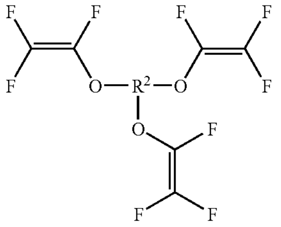

Via thermal cyclodimerization. The exothermic formation of the cyclobutyl linkages does not require catalysts or initiators nor does the polymerization produce condensates or by-products.

Two trifluoroviylidene-groups are able to react (thermally initiated) with each other under formation of a PFCB ring. Based on difunctional monomers, (thermoplastic) linear polymers are formed:

(IIa)

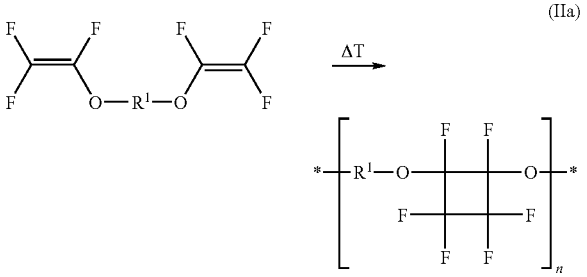

In the above PFCB monomers and polymers, $R^1$ and $R^2$ can be chosen from residues comprising or consisting of one, two or even more aromatic rings, the rings directly linked to each other or linked via —C—, —O—, —S—, $—SO_2—$, $—CR^{17}R^{18}—$, where $R^{17}$, $R^{18}$ are independently selected from optionally substituted alkyl groups or aryl groups. The aromatic ring(s) may contain one or more additional residues comprising other (functional) groups (e.g. —F, —Cl, —Br, —COOH, $NH_2$, $NO_2$ etc.).

Using at least trisfunctional monomers, the cycloaddition of the trifluorovinylidene-groups will yield a three-dimensional dense and crosslinked thermosetting polymer:

(IIb)

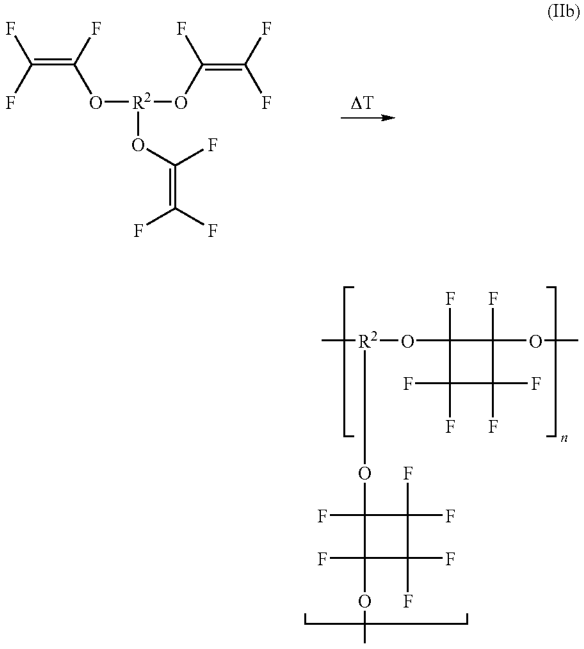

where $R^2$ is defined as in the formulae above.

Initially developed at The DOW chemical company, the general class of PFCB polymers was originally targeted for microelectronics applications.

By this unique fluoropolymer technology, based on perfluorocyclobutyl (PFCB) aromatic ether repeating units, materials are provided which exhibit thermo-mechanical robustness (e.g., $T_g$>200° C.) and solution processability. Perfluorocyclobutyl (PFCB) polymers and copolymers have demonstrated a superior combination of optical and structural properties including: low transmission loss, especially at the important telecommunication wavelengths around 1500 nm, unprecedented melt and solution or solventless processability, and tailorable refractive index and thermoptic coefficients. First generation PFCB optical polymer technology has been commercialized by Tetramer Technologies, L.L.C, Clemson, SC, USA.

The PFCB polymers show a number of outstanding properties, like high thermal stability, low optical loss, low dielectric constant, high transparency and good fracture stability, good fracture toughness and hardness.

However, depending on a particular application as desired, none of the said polymer classes is able to meet all requirements at the same time.

SUMMARY OF THE INVENTION

Thus, it is an object of the present invention to provide preparation routes for obtaining monomers containing at least one TFVE-group as well as at least one cyanato-group.

A further object of the invention is the synthesis of hybrid-like monomers via esterification of at least bifunctional phenols or OH-containing compounds with TFVE-group containing acid chlorides and subsequent cyanation with cyano halogen.

Further, it is an object of the present invention to provide a synthetic route for the preparation of homopolymers, starting from the said monomers.

Moreover, it is an object of the present invention to provide a method for the synthesis of copolymers of the novel hybrid-monomers and trifluorovinyloxyether-monomers and/or cyanate-monomers.

An additional object of the invention is to provide hybrid-like monomers, containing both, the trifluorovinyloxyether-group as well as the cyanato-group.

It is a further object of the invention to provide polymers from the said novel hybrid-monomers, as well as copolymers thereof in combination with cyanate-monomers.

Another object of the invention is the provision of new triazine containing (pre)polymers as well as a method for their preparation via esterification of OH-containing polycyanurates with TFVE-acid chlorides.

Finally it is an object of the present invention to provide monomers containing at least one TVFE group and at least one hydroxy group, as well as a method for the preparation of such monomers.

FIG. 2 is a schematic showing copolymerization of cyanates with fluorinated monools and diols.

FIG. 3 shows the structure of hyperbranched macromolecules that have a huge number of functional groups. The undulated lines stand for the different possible components corresponding to the different phenols, alcohols and/or cyanates; in the case of the present invention, the functional groups suitable for further reaction are remaining free OH-groups.

FIG. 4 shows the $^{19}F$ NMR spectrum of the product of Example 1.

FIG. 5 shows the $^{1}H$ NMR spectrum of the product of Example 1.

FIG. 6 shows the $^{13}C$ NMR spectrum of the product of Example 1.

FIG. 7 shows the $^{1}H$ NMR spectrum of the product of the Example 2.

FIG. 8 shows the $^{13}C$ NMR spectrum of the product of Example 2.

FIG. 9 shows the $^{19}F$ NMR spectrum of the product of Example 2.

FIG. 10 shows the $^{19}F$ NMR of the product of Example 3.

FIG. 11 shows the $^{1}H$ NMR spectrum of the product of Example 3.

FIG. 12 shows the $^{13}C$ NMR spectrum of the product of Example 3.

DETAILED DESCRIPTION OF THE INVENTION

In a first aspect of the present invention, novel compounds (hybrid-like monomers) are provided which contain at least one trifluorovinyloxyether (TVFE) group and at least one cyanato (—OCN) group. Preferably, the TVFE group of the said compounds is directly bound to an aromatic ring. More preferably, they are chosen from compounds of the following formula:

(III)

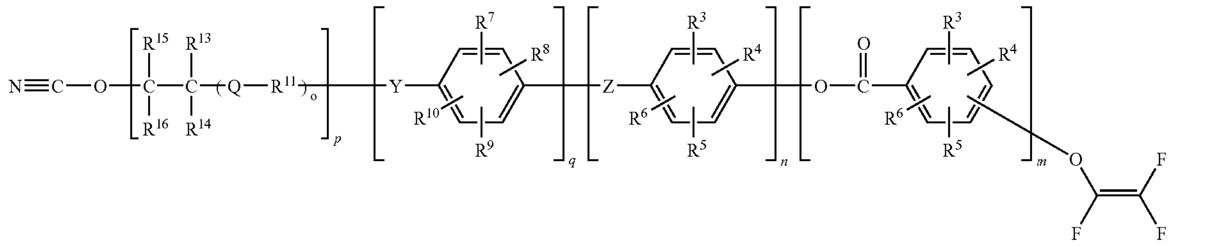

The synthesis of the hybrid-monomers can be carried out using different synthetic routes.

Surprisingly, it was found that hybrid-like monomers as described in the present invention can be prepared which contain reactive groups useful for each of the both polymer-classes described above on a molecular level. These hybrid-like monomers, containing both, the trifluorovinyloxyether-group as well as the cyanato-group, open the door to a huge number of new polymers, as both classes of monomers—respectively polymers—can be covalently bonded to each others.

Figure 1:
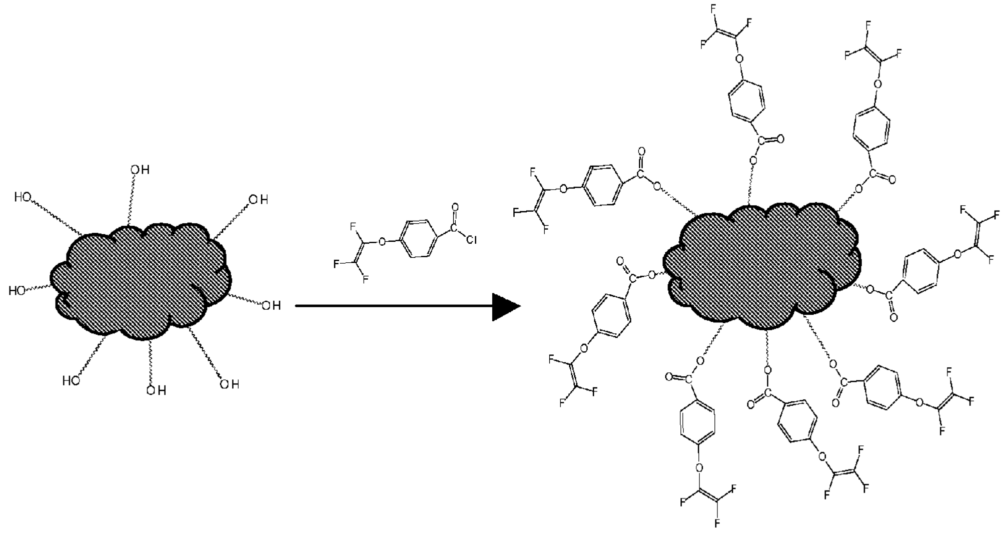
FIG. 1 illustrates the esterification of the OH-containing cyanurate-prepolymer with TFVE-acidchloride.

wherein the residues and indices are as follows:

$R^3$, $R^4$, $R^5$, $R^6$ can be independently chosen without restriction and are preferably independently selected among the following groups: —H, —F, —Cl, —Br, —I, —$CH_3$, —$CF_3$, —$(CH_2)_a$—$CH_3$, —$(CF_2)_a$—CF, wherein a is an integer which is preferably between 1 and 18, —$CH(CF_3)_2$, —$CF(CF_3)_2$, —$C(CH_3)_3$, -Ph, —$NO_2$, —$OCH_3$, —O—C(═O)—$R^{17}$ where $R^{17}$ is independently selected from optionally substituted alkyl groups or aryl groups, preferably having 1 to 8 carbon atoms, —OCN, wherein two of residues $R^3$, $R^4$, $R^5$, $R^6$ alternatively may together form a condensed aromate (e.g. naphthalene, anthracene, phenantrene). Alternatively or in addition, one or more of the groups $R^3$, $R^4$, $R^5$, $R^6$ can independently be selected from a cyanato group (—OCN), a trifluorovinyloxyether (TFVE) group (—O—CF═$CF_2$), residue

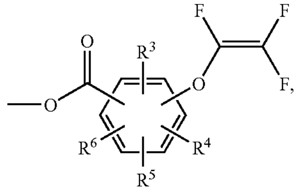

and preferably

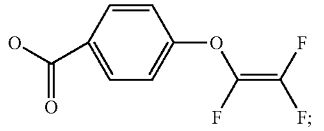

residues $R^7$, $R^8$, $R^9$, $R^{10}$ have the same meaning as defined for $R^3$, $R^4$, $R^5$, $R^6$ above, $R^{11}$ is a single bond or is an alkylene group which can be partly or fully fluorinated (i.e., the hydrogens of the alkylene can partly or fully be replaced by fluoro atoms), $R^{11}$ comprising preferably 1 to 30 carbon atoms, more preferably 1 to 8 carbon atoms and most preferably being $CH_2$, CHF, or $CF_2$, $R^{13}$ and $R^{14}$ both are preferably F, or $R^{13}$ is F and $R^{14}$ is H, (and only in less preferred embodiments, $R^{13}$ and $R^{14}$ are both H) or at least one of $R^{13}$ and $R^{14}$ is an optionally partly or fully fluorinated alkyl group preferably having 1 to 15 carbon atoms, and $R^{11}$, $R^{15}$ and $R^{16}$ can be either F or H, Y and Z are independent from each other and may be selected from a chemical bond, $SO_2$, $CF_2$, $CH_2$, CHF, $CH(CH_3)_2$, isopropylene, hexafluoroisopropylene, n- or iso-$C_1$-$C_{18}$ alkylene which may be partly or fully fluorinated, O, $NR^{19}$, N═N, CH═CH, —(C═O)—O—, —O—(C═O)—, CH═N, —C≡C—, CHN—N═CH, alkyloxyalkylene having 1 to 18 carbon atoms which is optionally partly or fully fluorinated, S, $Si(CH_3)_2$ or

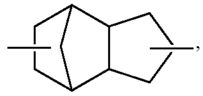, wherein $R^{19}$ is hydrogen or $C_1$-$C_{18}$ alkyl, wherein, if n and/or q is more than 1, either Y and/or z each can have different meanings within one molecule, Q can have the same meaning as Y and is preferably independently selected, if o is more than 1, under a chemical bond, —O—,

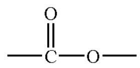 and 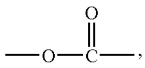, m is 0 or 1, n, in specific cases as detailed below, can be 0, but in all other cases is an integer, preferably 1, 2, 3, or 4, or even higher, preferably up to 6 o is 0 or an integer, preferably 1, 2, 3, 4, 5, 6, or even higher, preferably up to 12 p is 0 or 1, and q is 0 or an integer, preferably 1, 2, 3, or 4, or even higher, preferably up to 6.

It should be noted that the present invention also comprises compounds of formula (III) wherein the bonds which are depicted and drawn to be in para position to each other in formula (III) are instead partly or fully placed in meta or ortho position. The same applies to all other formulae throughout the specification.

In a first specific embodiment of the invention, m, p and q of formula (III) are zero, z is a chemical bond and n is 1. In this case, the compound of formula (III) will have the structure as depicted in formula (IV):

(IV)

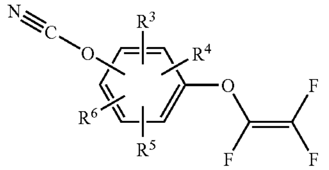

Compounds having formula (IV) are monoaromatic hybrid-monomers. In another specific embodiment of the invention, m and p are zero, q is 1, n is 1, and Y and Z each are a chemical bond. In this case, the compound of formula (III) will have the structure as depicted in formula (V):

(V)

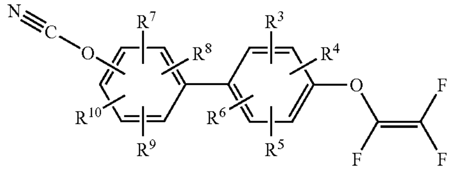

In still another embodiment of the invention, bisaromatic hybrid-like monomers are provided. In such cases, m and p will be zero, Y will be a chemical bond, while n is 1, 2, 3, or even more. Then, the compound of formula (III) may take the structure as depicted in formula (VI):

(VI)

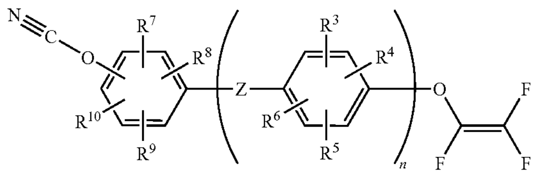

In still another embodiment of the invention, TVFE-substituted benzoic acid aromatic esters are provided, wherein the aromatic ester group contains at least one —OCN group. Such compounds can be derived from formula (III), wherein p is zero, and m is 1.

In a more specific embodiment thereof, in formula (III), p is 0, q is 1 m is 1 and Y is a chemical bond. Such compounds will be of general formula (VII):

(VII)

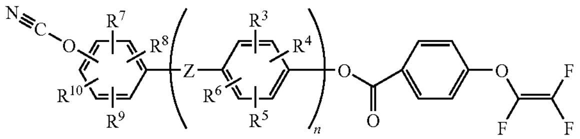

Of course, the aromatic ring of the benzoic acid may be additionally substituted. In such cases, that part of formula (VII) which reads

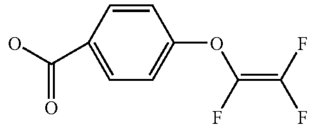

will be replaced by the following element:

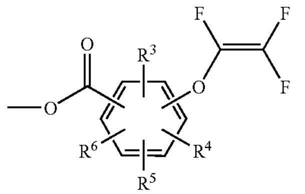

wherein $R^3$, to $R^6$ are defined as above for formula (III) and are preferably selected from the following groups:

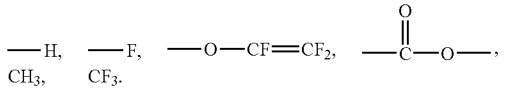

In an even more specific embodiment of this invention, compounds having formula (VII) are provided, wherein n is 0. The said compounds are of formula (VIII) below:

(VIII)

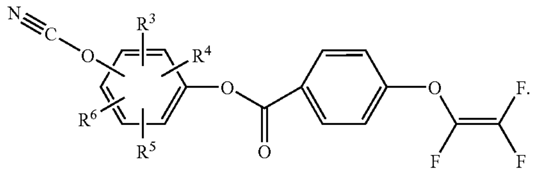

Of course, the aromatic ring of the benzoic acid may also in this case be additionally substituted, as outlined for formula (VII).

In another more specific embodiment of this invention, compounds having formula (VII) are provided, wherein n is 1, q is 1, and Y and Z both are chemical bonds. Such compounds are of formula (IX) below:

(IX)

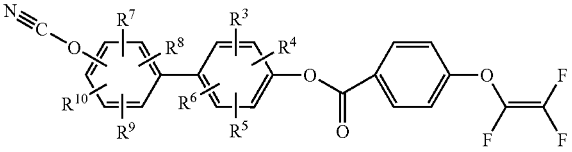

In this case, again, the aromatic ring of the benzoic acid may be additionally substituted as outlined for formula (VII).

In the embodiments of the present invention as detailed above, compounds are provided wherein not only the TFVE is directly bound to an aromatic ring, but also at least one OCN group. In alternative embodiments, this —OCN group is instead bound to an aliphatic residue.

The said alternative embodiments comprise compounds of formula (III) wherein p is 1. In preferred embodiments thereof, m is 1.

In one more preferred embodiment, o is 1.

In an even more preferred embodiment, Q is either a chemical single or, lesser preferred, double bond, or is

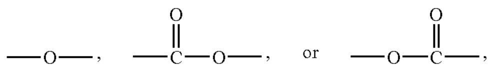

In most specific embodiments thereof, the said compounds can be derived from formula (III), wherein m is 1, p is 1, and q is zero. Then, the compounds of the present invention will be of formula (X):

(X)

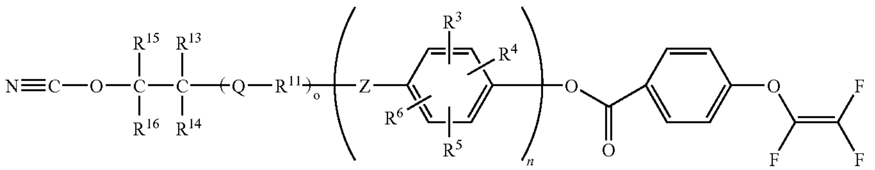

Again, the aromatic ring of the benzoic acid may be additionally substituted, as outlined with respect to formula (CII).

In formula (X), n is preferably 0, but can instead be 1, while o is preferably 1, but can—independently of the meaning for n—instead be 0 or 2, or can in specific cases be even higher In all of the compounds as defined above, the following embodiments are specifically and independently preferred:

None of $R^3$ to $R^{10}$ is a TVFE group.

None of $R^3$ to $R^{10}$ is a OCN group.

At least one of $R^3$ to $R^{10}$ is a TVFE group.

At least one of $R^3$ to $R^{10}$ is a OCN group.

At least one of $R^3$ to $R^{10}$ is

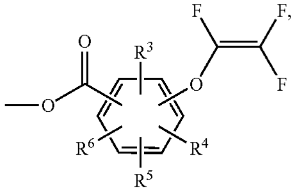

preferably

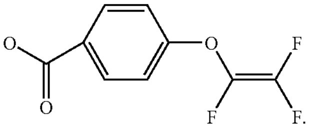

In a second aspect of the present invention, methods for the preparation of the compounds (hybrid monomers) as defined above are provided.

The synthesis of the hybrid monomeric compounds of the present invention can be carried out using a multiplicity of different routes. Generally speaking, the compounds may be prepared from TFVE containing halogenated or hydroxylated aromatic compounds or respective fluoroalcohols with at least one or more fluoro-atoms in 2-position by converting the hydroxyl substitutent of a respective hydroxylated compound into a cyanato group, wherein the hydroxy compound can have been obtained by previously converting the halo substitutent of a respective halogenated compound into a hydroxy group; or via Suzuki coupling, or via esterification reactions, as well as by combinations of the said reactions and/or previous and/or subsequent steps of conversion of substituents, especially of substituents of aromatic rings.

Suzuki coupling is a well known technique, see e.g. N. Miyaura, T. Yanagi, A. Suzuki, synthetic communications, 11(7), 513-519 (1981); H. W. Boone et al., 216th ACS Natianl Meeting in Boston, Polymer Preprings (Am. Chem. Soc., Div. Poly. Chem.) 1998, 39(2, 812, C. Griffiths and N. E. Leadbeater, Tetrahedron Letters 41 (2000) 2487-2490, or A. F. Littke et al., J. Am. Chem. Soc. 2000, 122, 4020-4028. Via this technique, it is possible to cross-couple phenylboronic acids with haloarenes. A necessary condition is the presence of a transition metal catalyst, usually a palladium catalyst, and alkaline (basic) conditions.

In a variety of cases, the synthesis will make use of an aromatic compound carrying at least one TFVE residue and one residue x, selected from OH, activated acid residue (preferably —C(O)Cl), Halogen (Cl, Br, and I, Br being preferred), —$B(OH)_2$OH, and —C(O)Cl, having formula (XI):

(XI)

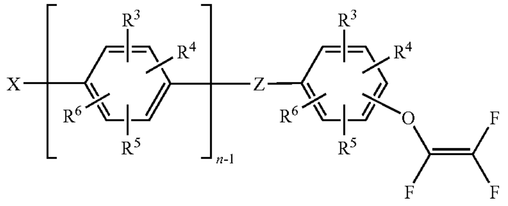

wherein $R^3$ to $R^6$, z and n are as defined above for formula (III).

Compounds having formula (XI), wherein X is a halogen, preferably By (formula XIa)

(XIa)

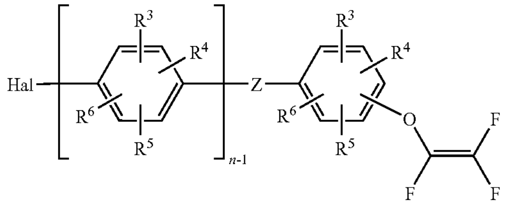

can be obtained, starting from a compound having formula (XII) wherein the residues and indices are as defined for formula (XI):

(XII)

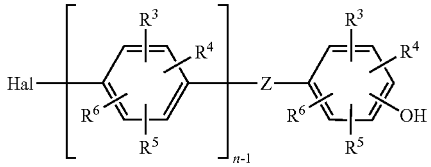

wherein the residues and indices are as defined in formula (III).

For this purpose, compound having formula (XII) is reacted in a first step with $HalCF_2CF_2Hal$ under alkaline conditions in a polar, preferably water-free solvent, wherein water formed during reaction is also preferably deleted, in order to urge the reaction balance to the side of the reaction product, and the product is then treated with Zn/MeCN (MeCN=acetonitrile. This reaction is preferably performed using Br as the halogen, and may be exemplified as follows:

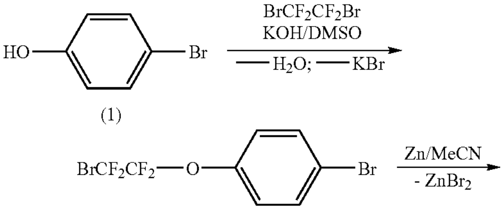

(1)

(2)

-continued

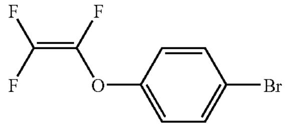

(3)

Thus, a phenolic compound (1) containing at least one OH-group and at least one abstractable group (Br—, Cl—, I—) is converted into the trifluorovinyloxyether compound (3) by a two step synthesis. These two steps are well described in literature and only shown for completeness.

Compounds having formula (XI), wherein X is —$B(OH)_2$, i.e. being of formula (XIb)

(XIb)

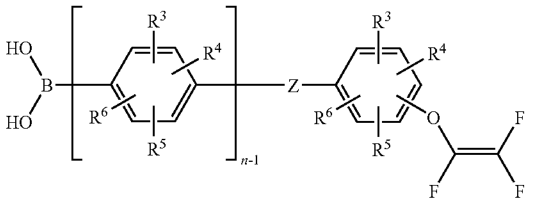

can be obtained from compounds having formula (XIa), by converting the halogen atom, preferably a Br atom, using t-butyllithium, $B(OMe)_3$ and HCl, preferably at temperatures around −78° C., resulting in a boronic acid. This reaction may be exemplified by the following scheme, depicting preparation of boronic acid (4):

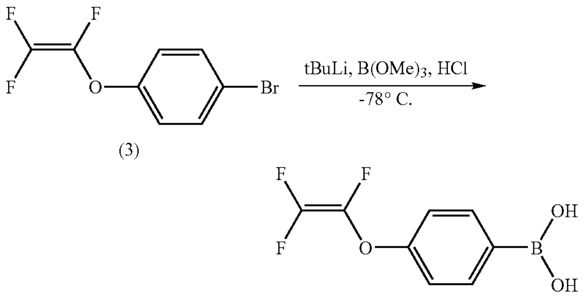

(3)

(4)

This reaction is well known to a skilled person; some boronic acids like that of formula (4) are commercially available.

Starting from formula (XIb), the boronic acid may be converted into a hydroxyl group, resulting in a compound having formula (XIc), wherein X is a hydroxyl group:

(XIc)

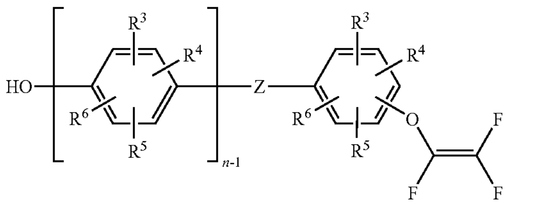

This conversion can be obtained using $H_2O_2$, as exemplified below:

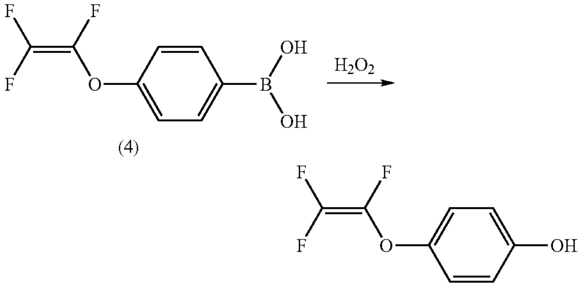

(4)

(5)

Starting from the halo compound having formula (XIa), an acid or activated acid derivative having formula (XId) can be obtained:

(XId)

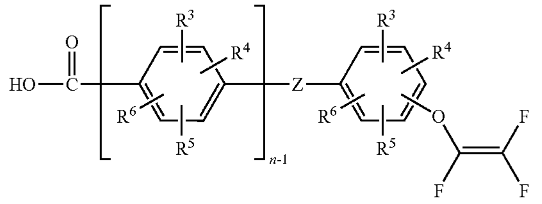

wherein V is Hal, preferably Cl, or is OH. This reaction is well known in literature and shall be exemplified by the following scheme:

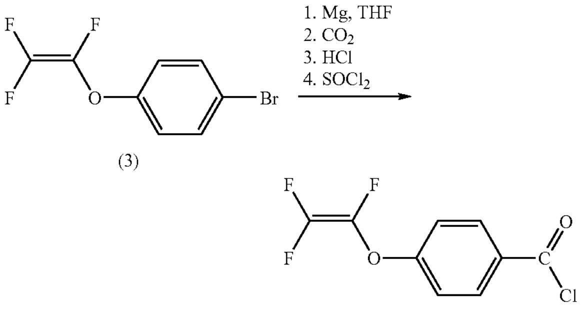

(3)

(6)

Cyanato compounds can easily prepared from respective hydroxy compounds, as known in the art. Thus, in order to obtain the compounds of the present invention, compounds having at least one free or protected hydroxy group may be coupled to TVFE containing compounds, followed by conversion of the free or deprotected hydroxy group into a cyanato group, or TVFE containing compounds may be prepared which are then reacted in order to introduce at least one hydroxy residue which is later converted into a cyanato residue. Therefore, starting with compounds of formula (XI) or (XII), a multiplicity of compounds of formula (III) can be obtained, as outlined below:

Route 1:

Starting from a compound having formula (XII), this compound is converted into compound having formula (XIa) as defined and exemplified above. Compound having formula (XIa) is then reacted with a boronic acid having formula (XIII), (XIII)

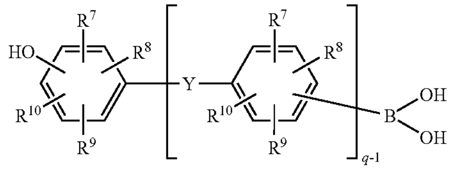

wherein the residues and indices are as defined in formula (III), via Suzuki coupling. This reaction scheme may be exemplified by the following:

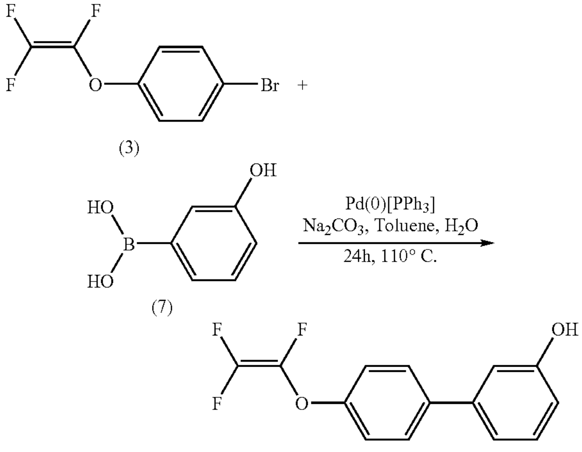

(3) (7) (8)

Boronic acid derivatives as (7) above can easily be prepared or are commercially available.

The product of this reaction, carrying a hydroxy residue, is then converted into the respective cyanato compound, using the well known cyanogen bromide (or cyanogen chloride, respectively) method which may be exemplified as follows:

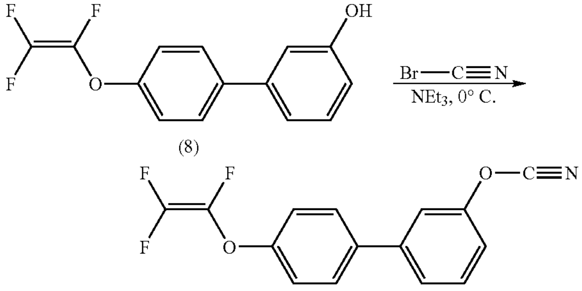

(8) (9)

The product will be a compound having formula (III), wherein p is zero. If in the starting compound of formula (XI) or (XII) n is zero, and in the starting compound of formula (XIII) q is zero, a compound having formula (V) will be obtained. Of course, compounds having formula (III) wherein either q is 1 (or, alternatively, is a higher integer) or n is 1 (or, alternatively is a higher integer), or wherein both q and n may be 1 (or, alternatively, a higher integer, independently selected), can likewise be prepared, starting from respective compounds having formulae (XI), (XII) or (XIII).

This includes that it should be obvious for a skilled person that instead of the compounds as depicted, analogous compounds with one ore more aromatic rings and/or with one ore more OH-groups and/or with at least one abstractable group (—Br, —Cl or —I) on different positions (isomers) can be used.

Rather than the respective boronic acid shown as compound (7), isomers thereof can be used. Further, boronic acids having two or more boronic-acid-groups could be used instead, as well as boronic acids having one or more aromatic rings and/or other functional groups or substituents.

Having also in mind the variability of Y and Z, it is therefore evident that a broad variety of compounds of formula (III) may be prepared by route 1.

The thus obtained hybrid-like monomers, can be homopolymerized or copolymerized with one ore more cyanato-containing monomers and/or trifluorovinyloxyether containing monomers and/or other hybrid-like monomers (cyanato- and trifluorovinyloxyether monomers), to obtain an broad range of new polymeric materials.

Route 2:

This route uses Suzuki coupling as well, but in an inverse manner: A compound having formula (XIa) in converted into compound having formula (XIb) as depicted and described above. This compound is then coupled to a haloaromatic compound having formula (XIV):

(XIV)

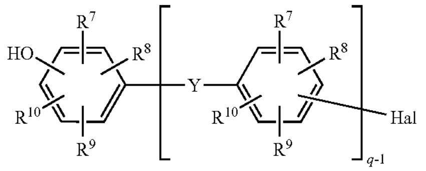

wherein the residues and indices are as defined in formula (III) and wherein Hal is Cl, Br, or I and preferably Br. The reaction may be exemplified as follows:

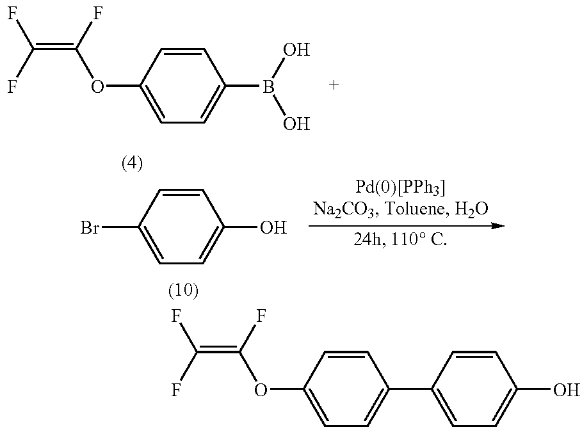

(4) (10) (11)

In a subsequent step, the OH-group of the product is converted into the respective cyanato compound, using the cyanogen halide method which may be exemplified as follows:

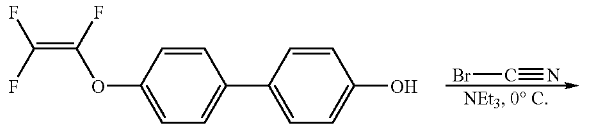

(11)

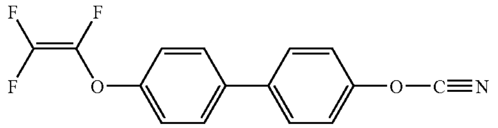

(12)

The product will be a compound having formula (III), wherein p is zero. If in the starting compound of formula (XIa) or (XIb), respectively, n is zero, and in the starting compound of formula (XIV) q is zero, a compound having formula (V) will be obtained. Of course, compounds having formula (III) wherein either q is 1 or a higher integer, or n is 1 or a higher integer, or wherein both q and n may independently be selected from 1 or a higher integer, can likewise be prepared, starting from respective compounds having formulae (XI), XII) or (XIII).

This includes that it should be obvious for a skilled person, that instead of the compounds as depicted, analogous compounds with one ore more aromatic rings and/or with one ore more OH-groups and/or with at least one abstractable group (—Br, —Cl or —I) on different positions (isomers) can be used.

Rather than the respective bromo-phenol shown as compound (10), isomers thereof or variety of different phenols could be used. Further, phenols with one or more bromine-atoms could be used instead, as well as phenols comprising one or more aromatic rings and/or other functional groups or substituents. Moreover, compound (10) could be replaced through phenols having two or more OH-groups or by compounds carrying combinations of the mentioned functional groups.

Therefore, also route 2 is suitable for the preparation of a broad variety of compounds of formula (III), specifically when bearing also in mind the variability of Y and Z.

The thus obtained hybrid-like monomer can be homopolymerized or copolymerized with one ore more cyanato-containing monomers and/or trifluorovinyloxyether containing monomers and/or other hybrid-like monomers (cyanato- and trifluorovinyloxyether monomers), to obtain a broad range of new polymeric materials.

Route 3:

As mentioned above, it is possible to convert hydroxy compounds into the respective cyanato derivatives via the so called halogencyan method. Starting from boronic acid derivatives having formula (XIb), it is therefore possible to obtain compounds having formula (III) wherein p is zero and q is zero, directly via conversion of said boronic acid derivatives into the respective hydroxy derivatives having formula (XIc), using hydrogen peroxide, as detailed above, and to convert the hydroxy residue thereof into the cyanato residue by using the halogencyan-method. This reaction scheme shall be exemplified below:

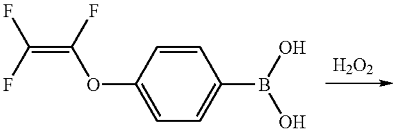

(4)

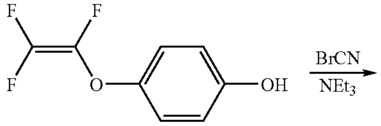

(13)

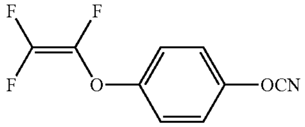

(14)

It will be evident for a skilled person that this route does not only provide the possibility to obtain compounds which may also be obtained via routes 1 and 2, but also to obtain compounds having only one aromatic ring. Such compounds are not available via Suzuki coupling.

Thus, depending on the starting material having formula (XIb) or (XIc), respectively, using the method for the preparation of the hybrid compounds of the present invention according to route 3 any compound having formula (XIe) can be obtained (XIe)

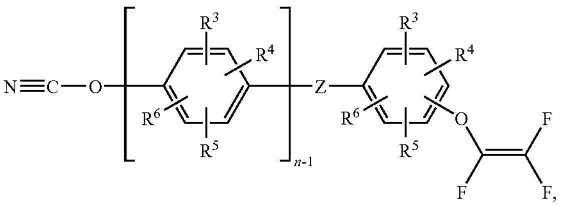

wherein the residues and indices are as for formula (XI), and specifically, this route is suitable for the preparation of compounds having formula (IV).

Therefore, it will be apparent for a skilled person, this method is suitable to prepare not only compound (14) as depicted above, but, instead thereof, analogous compounds having one ore more aromatic rings and/or having one ore more OCN residues on different positions (isomers). Further, such compounds may carry one or more TFVE residues (i.e., one or more of residues $R^3$ to $R^6$ may be a TFVE residue and/or a OCN residue).

Route 4:

The above methods for the preparation of compounds having formula (III) either use Suzuki coupling in order to couple selected parts of the molecule (routes 1 and 2) or start with a molecule the backbone of which being already as in the final product (route 3). Instead, it is of course possible to combine different parts of the molecule via other "classical" reaction methods, e.g. esterification of alcohols with carbonic acid molecules, the latter ones preferably being activated such that they are able to react with free alcohol groups.

In order to perform such an esterification reaction. the starting acid molecule or molecule having an activated acid group will conveniently be of formula (XId). The alcohol molecule reacting therewith may either be aromatic or aliphatic and will preferably be selected from difunctional (divalent) alcohols.

Route 4 uses the above mentioned esterification reaction, wherein the alcoholic components are selected from aromatic, aliphatic, and mixed aliphatic-aromatic compounds. More preferably, it may be selected from the group consisting of aromatic compounds having formula (XV):

(XV)

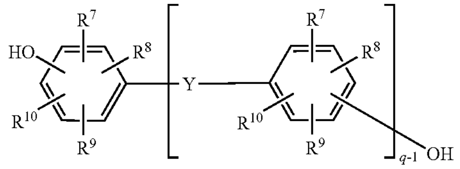

wherein the residues and indices are as defined in formula (III), and from aliphatic compounds having formula (XVI):

(XVI)

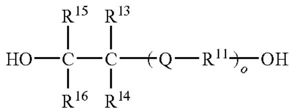

wherein the residues and indices are as defined in formula (III).

Therefore, the compounds obtained therewith will either provide compounds of formula (III) wherein m is 0, p is 0, and at least one z is —OC(O)—, or will provide molecules having formula (III) wherein m is 0, q is 0, and at least one z is —OC(O)—.

In specific cases, namely if a compound of formula (XId) is used wherein n is 1, the compounds obtained may alternatively be depicted by formula (III) wherein m is 1, n is zero and either p or q is zero.

In order to obtain compounds having formula (XId), it is preferred to start with compounds of formula (XIa), and more preferred to start with bromo derivatives thereof. Such compounds are easily available from compounds of formula (XII), as outlined above.

Compounds of formula (XV) (e.g. compound (15) below) can be esterified with compounds of formula (XId) (e.g. compound 6 below), preferably using the starting materials in equimolar amounts. This reaction will result mainly in a product wherein compound (XId) maintains its second hydroxy residue in free form. This is due to the fact that the reactivity of phenolic hydroxy groups of multifunctional phenols gradually decreases, i.e. the reactivity of the second OH group is reduced after the first has been esterified. This will result in a first step which is the formation of a monoester like that designated as (16) below, which in turn can be converted into the hybrid monomer (17) using cyanogenbromide:

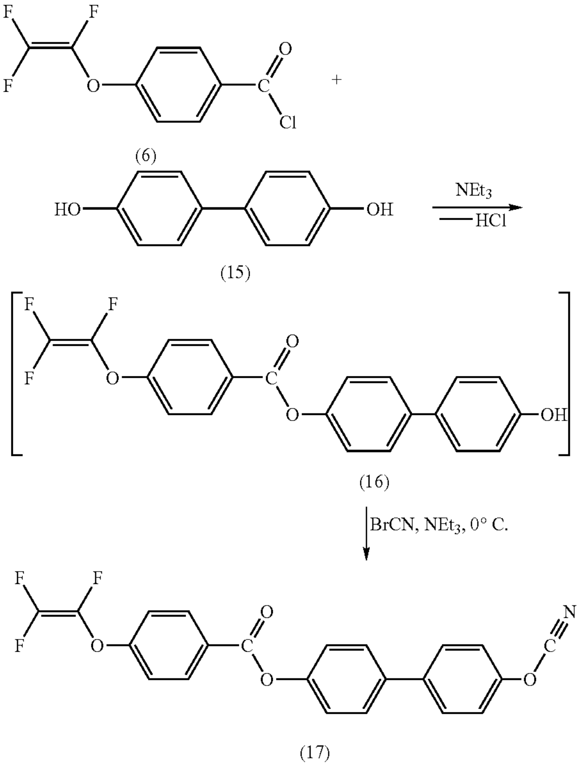

The above reaction is the "ideal" conversion. Side reactions, due to an esterification of the second hydroxy group of compounds having formula (XV), might however sometimes occur. In such a case, trifluorovinyloxyethyl-diester compounds and dicyanate compounds will be the side products. A purification of such a product mixture can be easily performed, e.g. via chromatographic procedures which are well known to one skilled in the art.

Using different di- or even higher functional phenols or other aromatic bis- or even higher functional alcohols, a huge number of compounds having formula (III) wherein m is 1 and p is zero may be obtained. For example, compounds having formula (IX) can be achieved via this esterification route, starting from a compound of formula (XId) wherein n is 1 and Z is a chemical bond, and from a compound of formula of formula (XV) wherein q is 2 and Y is a chemical bond. Residues $R^3$ to $R^{10}$ will have the meaning as defined for formula (III). In specific cases, at least one of said resides will have the following meaning:

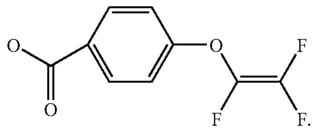

Instead, compounds having formula (VII) can be obtained, starting from a compound of formula (XId) wherein z is a chemical bond and n is 1, and from a compound of formula (XV) wherein q is at least 2 and Y is replaced by z. (It should be clear from the above that Y and Z are independently be selected from the same group of residues). Residues $R^3$ to $R^{10}$ will have the meaning as defined for formula (III). In specific cases, at least one of said resides will have the following meaning:

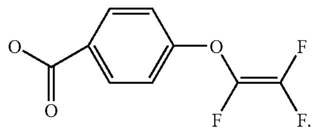

If a compound having formula (XId) as defined above is combined with a compound of formula (XV) wherein q is 1, compounds of formula (VIII) can be obtained, wherein the substituents are defined as for the compounds having formula (III) above, except that $R^3$, $R^4$, $R^5$, $R^6$ may independently be also selected from:

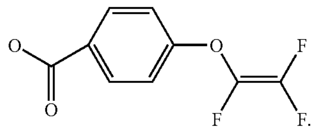

Instead, starting from compounds of formula (XVI) and not from compounds of formula (XV), the reaction with compounds of formula (XId) will result in compounds having formula (III) wherein p is 1 and q is zero. In specific cases, namely if a compound of formula (XId) is used wherein n is 1, the compounds obtained may alternatively be depicted by formula (III) wherein m is 1.

Further, partly aliphatic and partly aromatic compounds can be obtained via esterification route 4, namely if a compound having formula (XVII), wherein the residues and indices are as defined in formula (III), is employed instead of compound (XVI), and is reacted with a compound of formula (XId) wherein n is 0.

(XVII)

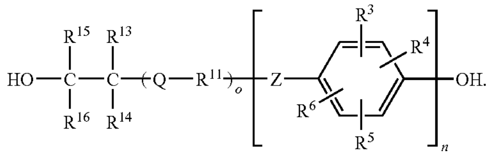

Therefore, compounds of formula (X) may be obtained by this route.

Route 5:

This route results in new hybrid (pre)polymers (TFVE-terminated polycyanurate ester resins) obtained via two step synthesis. In contrast to routes 1-4, no hybrid-like monomer is formed. In a first step, OH-containing polycyanurate ester resins are synthesized as described below.

Step 1: Synthesis of OH-Containing Polycyanurate Ester Resins.

Cyanates can be copolymerized with fluorinated or partly fluroinated monools, diols and/or polyols, e.g. of the below formula,

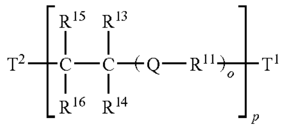

wherein either $T^1$ or $T^2$ both are OH, or only one of residues $T^1$ or $T^2$ is OH, while the other one can be selected from TFVE, H, F or alkyl, while the other residues and integers are defined as for formula (III), and/or with mono, di and/or polyfunctional phenols, e.g. of the general formulae below, wherein $T^1$ and $T^2$ are defined as for the aliphatic alcohols above, while the other residues and integers are defined as for formula (III):

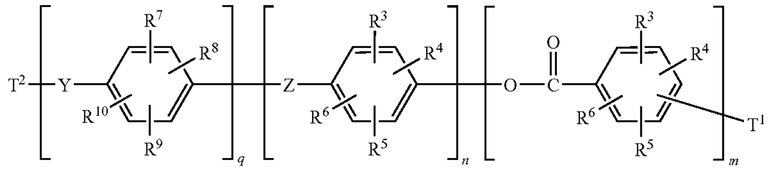

Figure 2:
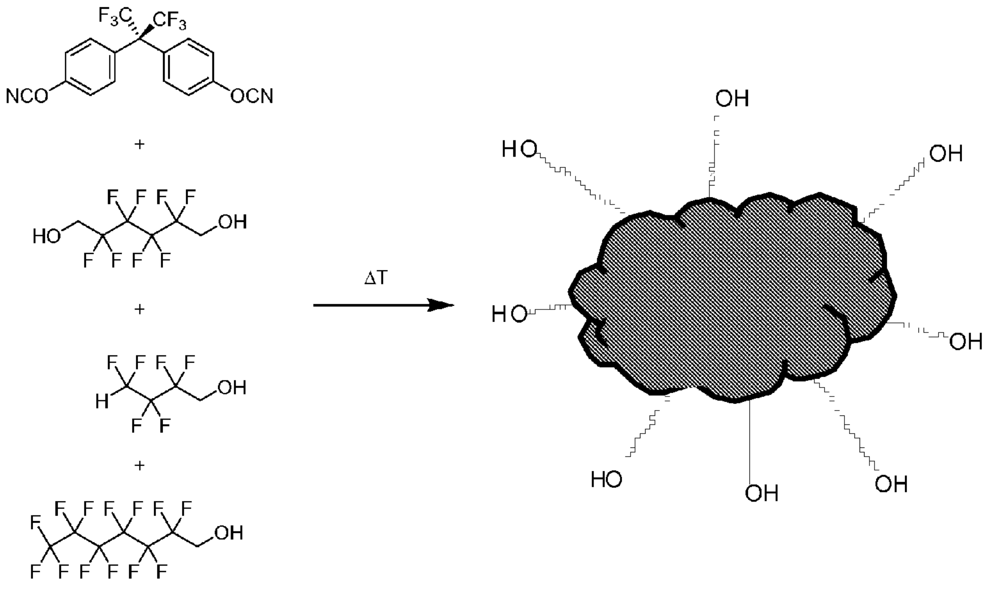

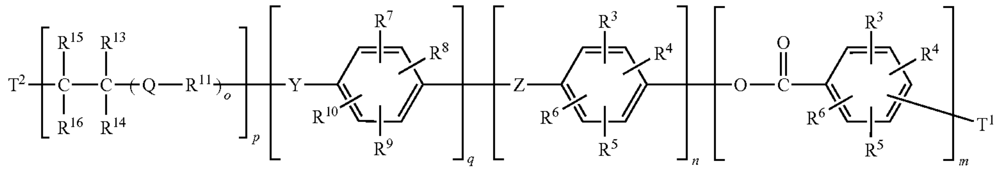

wherein, in specific embodiments, at least one of residues $R^3$, $R^4$, $R^5$, $R^6$, $R^7$, $R^8$, $R^9$, and $R^{10}$ can also be OH, via thermal polymerization in bulk or in solution. The mechanism is depicted in FIG. 2. Partly, this reaction is known from prior art which is herewith incorporated by reference.

The macromolecules obtained in such a way can be used in different applications, as they are soluble in common organic solvents and the viscosity of the solutions can be adjusted by using different concentrations.

Figure 3:
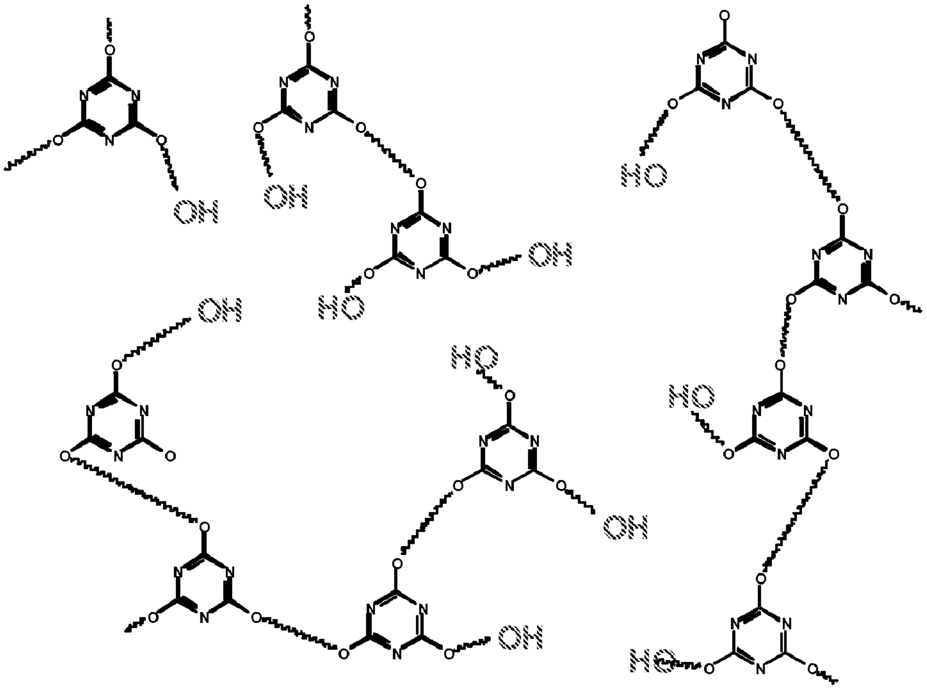

Said macromolecules can be regarded as hyperbranched compounds. They have a huge number of functional groups (primarily in the outer sphere). In the case of the present invention, the functional groups suitable for further reaction are remaining free OH-groups. FIG. 3 shows the structure of these macromolecules. The undulated lines stand for the different possible components (corresponding to the different phenols, alcohols and/or cyanates).

Step 2: Esterification of Free OH Groups

In a second step, the OH-terminated polycyanurate ester resin obtained by step 1 can be esterified using compounds of formula (XId) in a comparable way to that outlined above under route 4, provided that it is soluble in at least one of organic solvents commonly used for esterification. The reaction is exemplified in FIG. 1.

The resulting TFVE containing cyanurate is soluble in common organic solvents and may therefore be e.g. spin-coated, blade-coated, casted into thin films for use in different applications. Further, it is possible to prepare prepregs, laminates, composite materials (containing fillers) and the like, using the materials of the present invention, and to subject such articles to a subsequent thermoplastic processing and/or deformation (e.g. extrusion).

Depending on the number of cyanato-groups and on the reactivity of the cyanates and also of the reactivity of the OH-containing starting material compound (respectively the phenols or fluoroalcohols), the said TFVE containing cyanurates can be cured as known for a skilled person. The resulting polymer may form a highly dense network, as far as all the cyanato-groups contained are converted. This is the case if smaller ratios of OH-containing compounds to OCN containing compounds are used for the copolymerization of step 1. Above a certain upper limit of OH-containing compounds in said copolymerization, no gelation can be observed. Then, the resulting product cannot be regarded as one huge polymer, but will consist of a distribution of (smaller) macromolecules which are soluble in appropriate solvents. Increasing the OH-content by using larger amounts of OH containing compounds for the said copolymerization reaction will result in lower molecular weights of the resulting macromolecules.

Polymers

Synthesis of (homo)polymers and copolymers of the hybrid monomers of formula (III) as well as synthesis of polymers and copolymers of the TFVE-terminated polycyanurate ester resins, obtained according to route 5, is also possible:

Homopolymers

The hybrid-like monomers of the present invention, especially those of formulae (III), and preferably those of formulae (IV), and (V), (VI), (VII), (VIII) and (IX) may be homopolymerized in bulk or in solution at appropriate temperatures (typically above room temperature, e.g. 130-190° C., depending on the particular hybrid-like monomer). By stopping the reaction before gelation (e.g. using liquid nitrogen to quench the polymerization of bulk materials), meltable and soluble prepolymers can be obtained, which can be used for different applications, described below.

Copolymers with Cyanurates

The hybrid-like monomers of the present invention, especially those of formulae (III), and preferably those of formulae (IV), (V) and (VI), can be copolymerized with at least one cyanate compound, carrying one or more cyanato-groups. The cyanate compounds may be freely selected and are preferably of formula

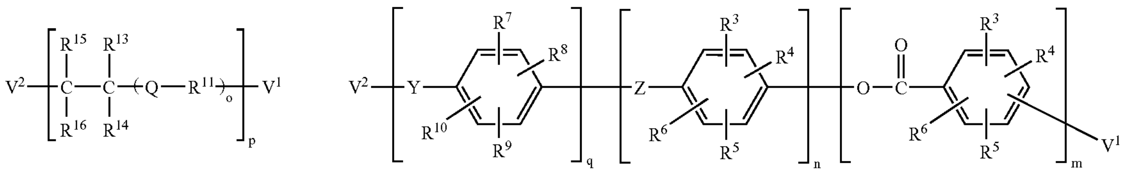

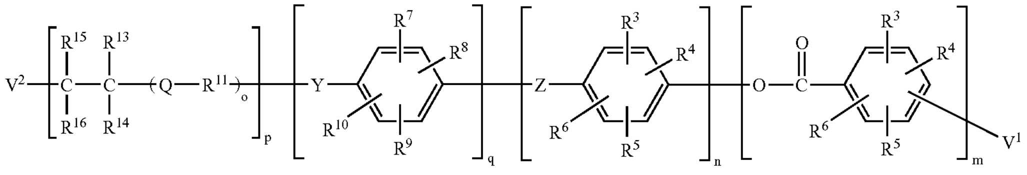

wherein either $V^1$ or $V^2$ both are —OCN, or only one of residues $V^1$ or $V^2$ is —OCN, while the other one can be selected from H, F, or alkyl, and the other residues and integers are defined as for formula (III). These molecules should preferably be free of TFVE and hydroxy residues.

The syntheses are carried out as described for step 1 of route 5. Depending on the particular hybrid monomer and on the particular cyanate(s), the properties of the resulting copolymer can be adjusted in a broad range.

Applications

The homo- and copolymers described above can find a wide range of applications, for example: waveguide materials for (integrated) optics, protective coatings, optical coatings, adhesives, substrate materials for integrated optical devices and/or microelectronic devices, low-k materials, underfiller, matrix-materials for composite materials, material for other optical applications (lenses, prisms, cylinders, polymer optical fibers, using for hot embossing and LIGA-technology, for automotive and aeronautic and outer space applications, barrier layers or the like.

The homopolymers and copolymers as described above are used especially to make thin layers, coatings, barrier-layers, bulk-material, fiber-reinforced composites, preferably a glass-fibre, aramide, natural fiber, carbon-fiber, an adhesive, low-k material, fiber, or fiber for light guiding.

The homopolymers and copolymers as described above are especially used to make an optical waveguide, preferably selected from mono-mode and multi-mode waveguides, an optical grating, or an integrated optical device.

The homopolymers and copolymers as described above are especially used to make via reactive ion etching (RIE) or micromolding an optical component, an optical waveguide, preferably selected from mono-mode and multi-mode waveguides, an optical grating or an integrated optical device.

The homopolymers and copolymers as described above are especially used to make an optical component, preferably selected from prisms, lenses, fresnell lenses, substrate materials, preferably for microelectronics, integrated optical devices.

The homopolymers and copolymers as described above are especially used to make a prepreg, laminate, composite material containing at least one filler, optionally by being subjected to a subsequent thermoplastic processing and/or deformation or extrusion.

EXAMPLES

Example 1

Corresponding to Route 1

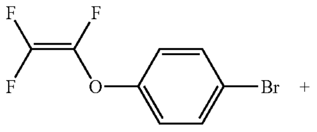

(3)

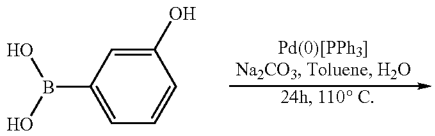

(7)

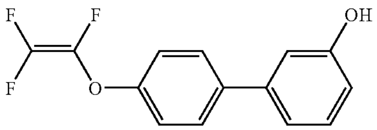

(8)

Figure 4:
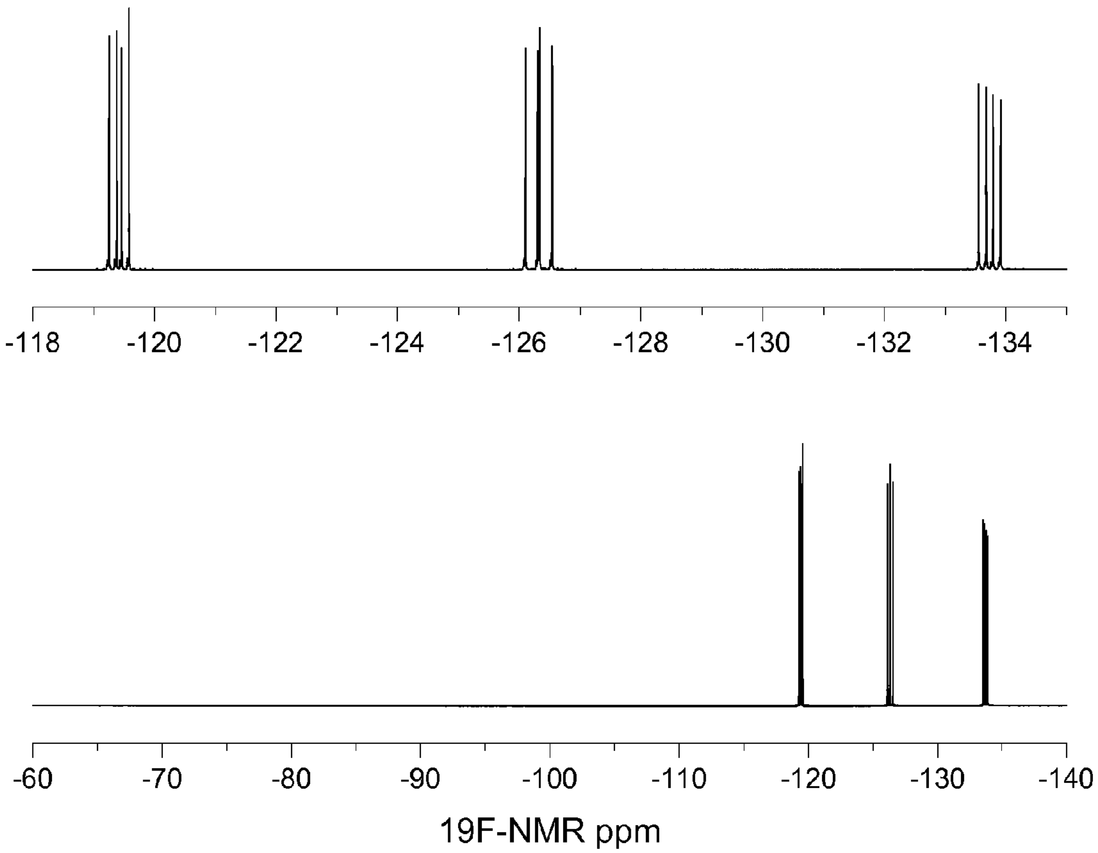
Figure 5:
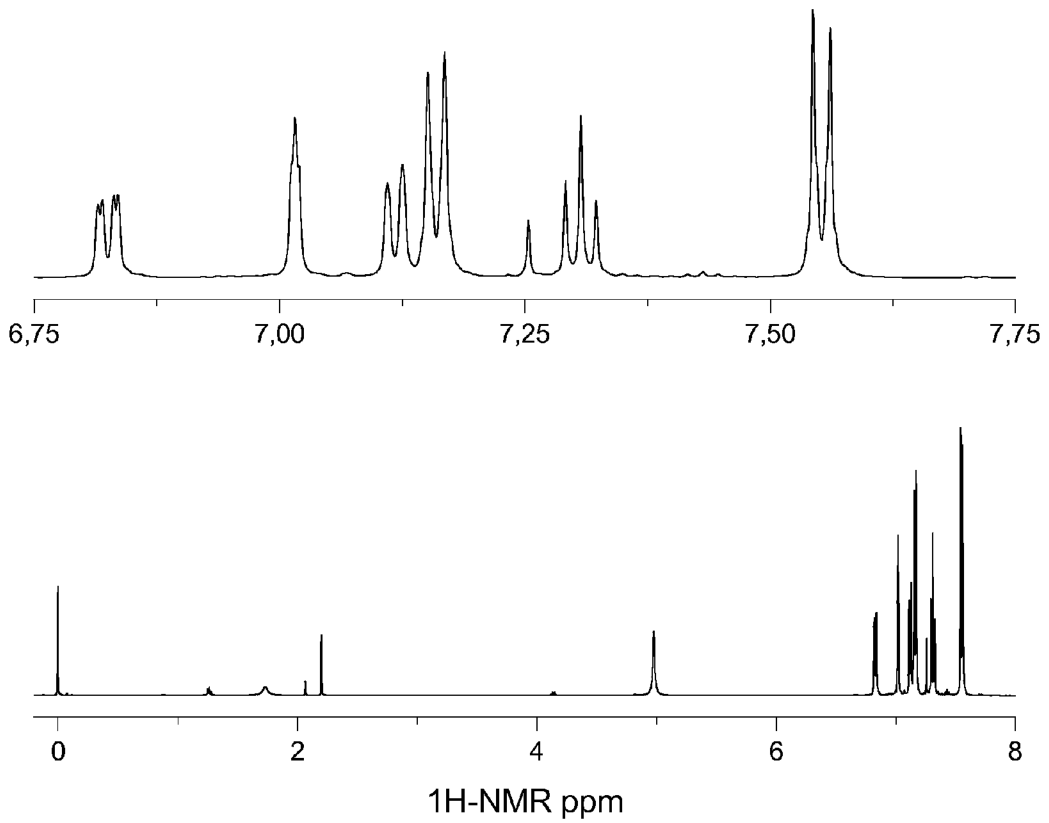
Figure 6:
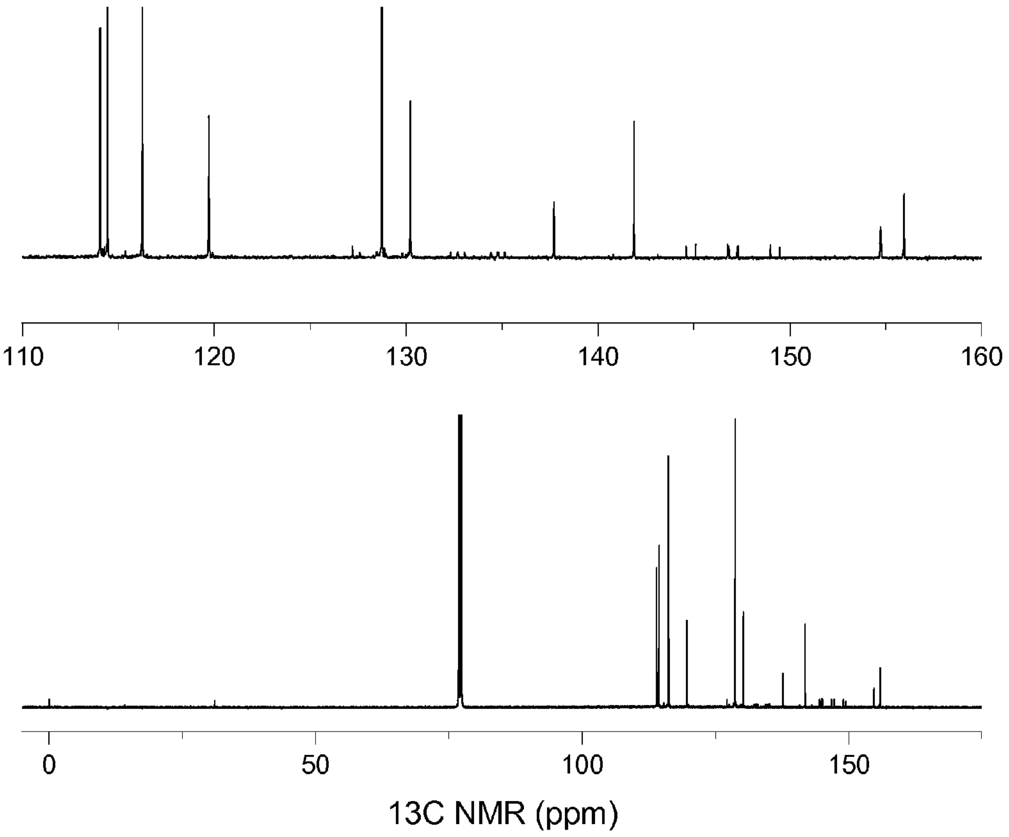

1.771 g (7 mmol) of the bromo-TFVE compound (3) (MW=253 g/mol) (commercially available from Tetramer LLC, Clemson) and 276 mg (0.24 mmol) tetrakistriphenylphosphine)-Palladium(0) (99%) are dissolved in a mixture of 20 ml of Toluene, 7 ml of Ethanol and 7 ml of 2M $Na_2CO_3$-solution in a three neck flask with condenser under Nitrogen. 1.545 g (7 mmol) of the 3-Hydroxyboronic acid (7) (commercially available) are added to the mixture. The color of the mixture changes to dark red. The mixture is stirred under reflux for approx. 24 h. The mixture is cooled down to room temperature and 40 ml of $CH_2Cl_2$ and 20 ml of water are added and poured into a separation funnel. The aqueous phase is extracted three times with 30 ml of $CH_2Cl_2$. The combined organic phases are reextracted with sodium chloride solution and dried over $MgSO_4$. The filtered solution is concentrated by using a rotavap. The purification of the crude product is done by flash-cromatography using a Hexane/Ethylacetate mixture. The determination of the purity of the fractions is done via TLC and GC-MS. 0.637 g (2.39 mmol) of a pale yellow crystalline solid are obtained after removal of the solvent with a purity of >95% (GC-MS); yield: 34.1%. In addition to GC-MS, characterization of the compound obtained was done via $^{19}F$ (FIG. 4), $^{1}H$ (FIG. 5), and $^{13}C$ (FIG. 6) NMR. In the next step, compound 8 is converted into the corresponding TFVE-cyanate hybrid monomer 8 as shown in example 2.

Example 2

Corresponding to Route 1

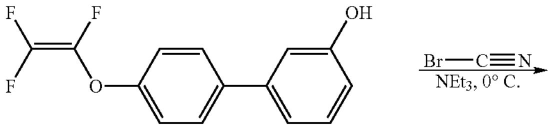

(5)

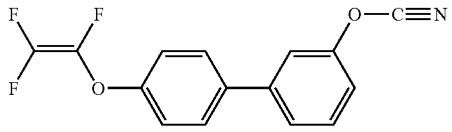

(9)

199.5 mg (0.75 mmol) of the TVE containing phenol (8) and 106 mg (1 mmol) cyanogen bromide are dissolved in 10 ml of chloroform. 10 ml water are added. The mixture is cooled down to 0° C. 76 mg (0.75 mmol) of $NEt_3$ are dissolved in 3 ml of chloroform and added during 10 minutes into the reaction mixture under vigorous stirring. The temperature rises up to +1° C. The organic phase is separated. The aqueous phase is washed twice with chloroform. The unified organic phases are washed 1× with sodium carbonate solution and 2× with water. The solution is dried over $MgSO_4$; after filtration the chloroform is removed via vacuum distillation. 210 mg of yellow oil are obtained (yield approx. 96.3%). The GC-MS chromatograph shows 13% of a byproduct (MW 272). Further purification can be done by recrystallization.

Figure 7:
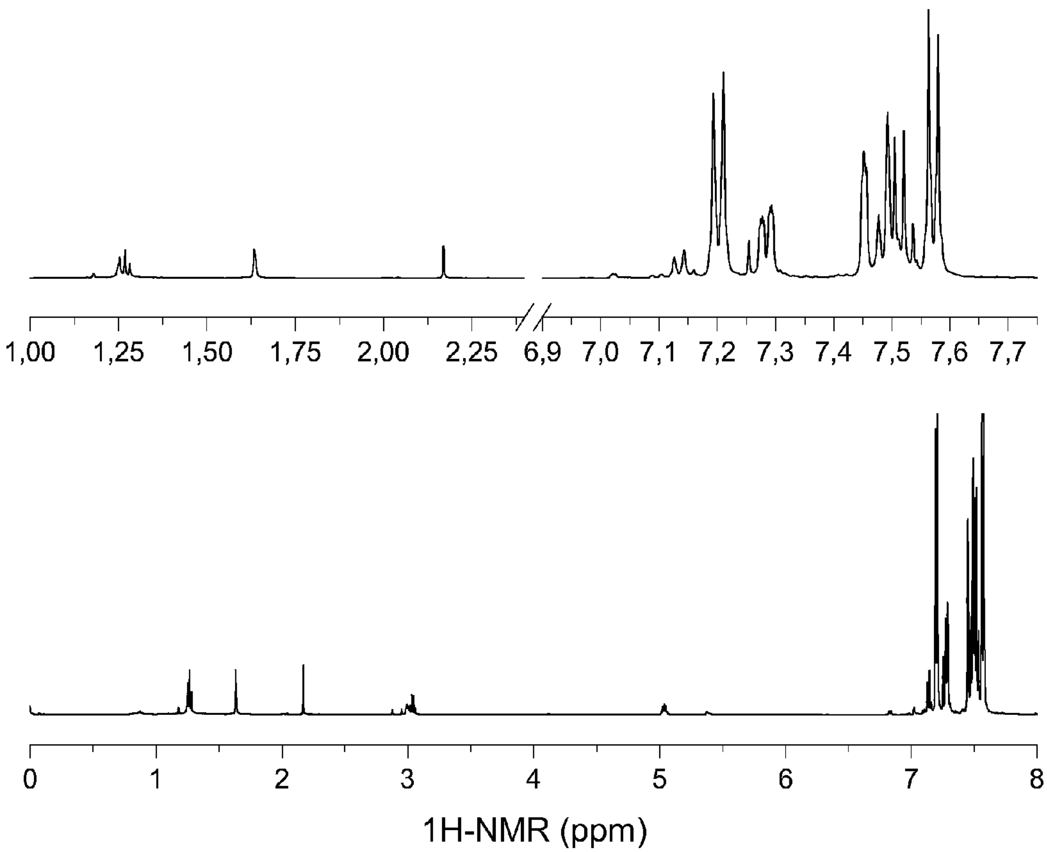
Figure 8:
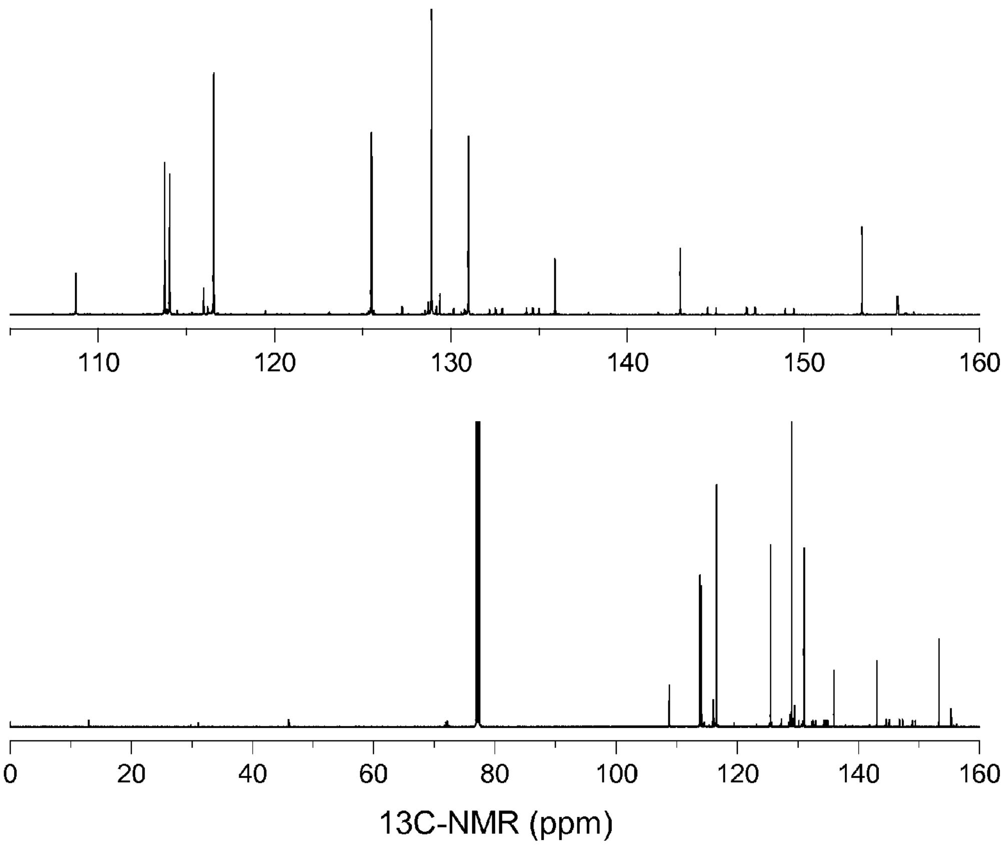
Figure 9:
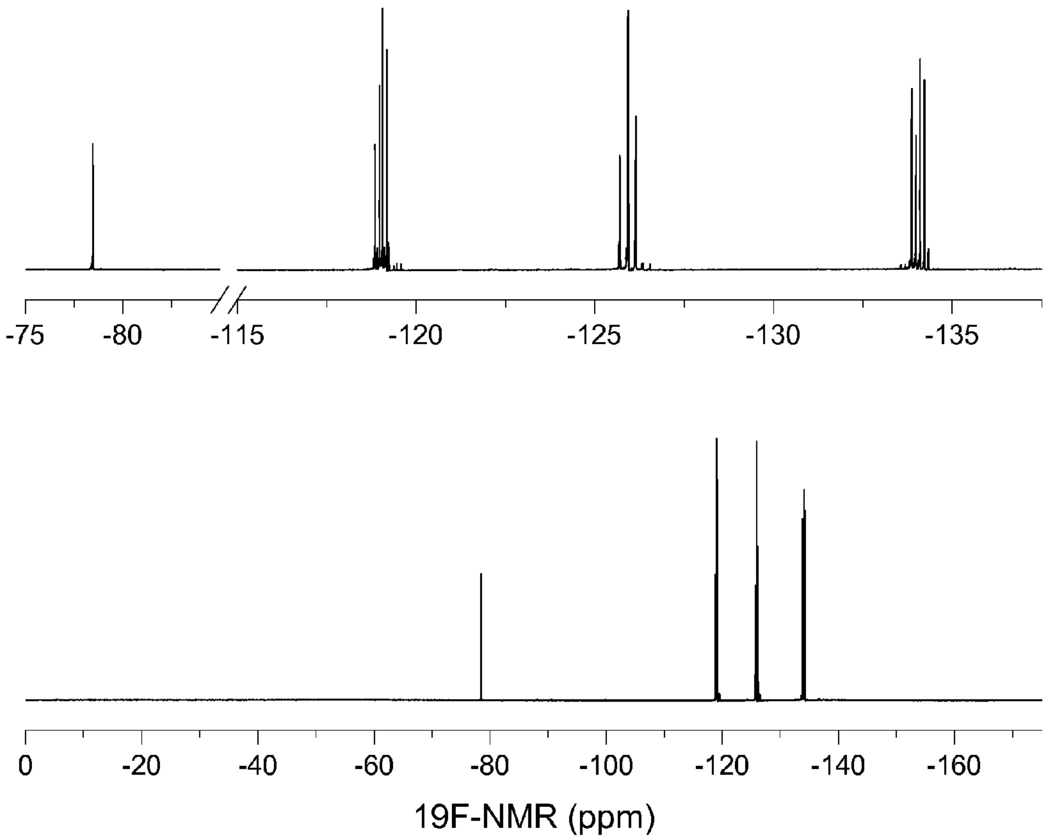

The successful reaction was proved via GC-MS. Further, $^{1}H$ (FIG. 7), $^{13}C$ (FIG. 8) and 19F- (FIG. 9) NMR-spectroscopy was done.

Example 3

Corresponding to Route 2

The bromo-trifluorovinyloxyether-benzene 3 is converted into the corresponding boronic acid 4 as described below:

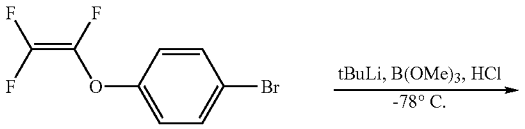

(3)

-continued

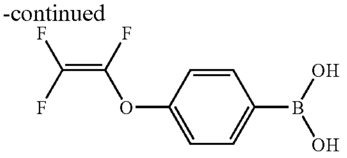

(4)

In a 500 ml three neck flame dried flask equipped with a nitrogen inlet and a rubber septum were 20.24 g (80 mmol) of the Bromo-TVE dissolved in approx. 160 ml of dry diethyl ether. The solution is cooled down using an acetone/liquid-nitrogen bath. 58.7 ml of an 1.5 M solution of tBuLi in pentane (88 mmol) were added dropwise during two hours. The now turbid solution is stirred for another hour at −78° C. 10.05 ml (88 mmol, 9,144 g) were added dropwise during 30 min. The mixture is allowed to defrost overnight. The reaction mixture is quenched with approx. 100 ml 5 N HCl and 50 ml $H_2O$. Workup is done via extracting 3× with HCl and 1× with saturated sodium chloride solution. The organic phase is dried over $MgSO_4$ and the solvent is removed using a rotavap. 10.3 g (mmol) of a dirty white solid (4) were obtained. Yield: 59.1%. The product was identified, inter alia via $^1$H-NMR spectroscopy.

The next step, the formation of the OH-TFVE-monomer 11 was done via Suzuki-coupling:

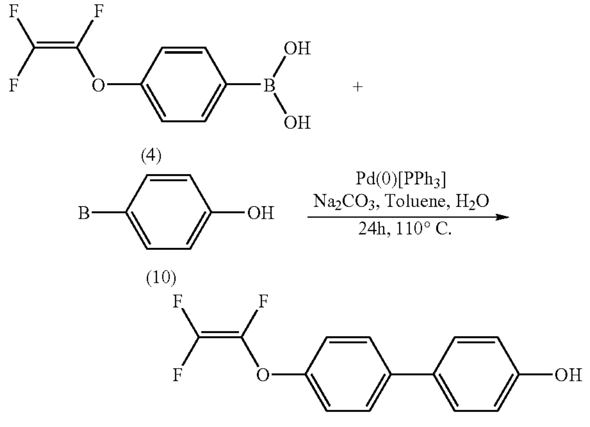

(4)

(10)

(11)

To a solution of 7 mmol (1.211 g) of 4-bromophenol in 20 ml toluene and 4 ml of ethanol, in an 50 ml 3-neck-flask equipped with a condenser and a nitrogen inlet 7 ml of a 2M NaOH-solution (14 mmol) were added. To the slightly rosy solution were added 0.24 mmol (276 mg) of $Pd(PPh_3)_4$ resulting in a color change into yellow. 7 mmol (1.526 g) of the TVE containing boronic acid 4 were added to the mixture. The mixture was heated to reflux, resulting into a color change into dark red. The reaction mixture was allowed to stir under reflux for 27 h. saturated NaCl-solution was added to the dark red liquid. The toluene-phase was removed and the aqueous phase was extracted three times with dichloromethane. The unified organic phases were dried over $MgSO_4$ and the solvent was removed. 1.36 g of the reddish crude solid product were obtained. Yield ≈75%. The purification was done by using a silica-column (25 cm silica) and a hexane/ethylacetate mixture as the mobile phase. After removing of the solvent ≈500 mg of pale yellow crystals were obtained. Yield: 26.9% Two byproducts were identified via 19F-NMR. The purity of the product 11 is ≈93%.

The OH-TFVE-monomer 11 can be converted into the corresponding cyanate analogous to Example 2.

Figure 10:
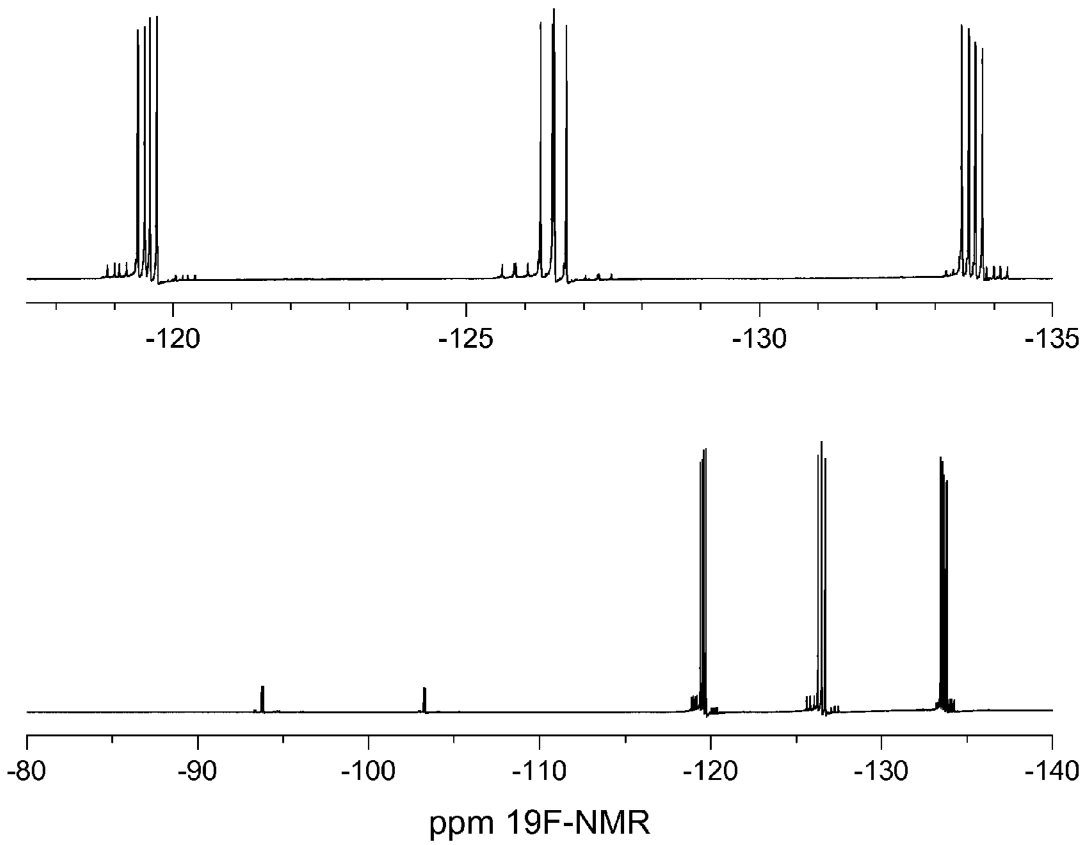
Figure 11:
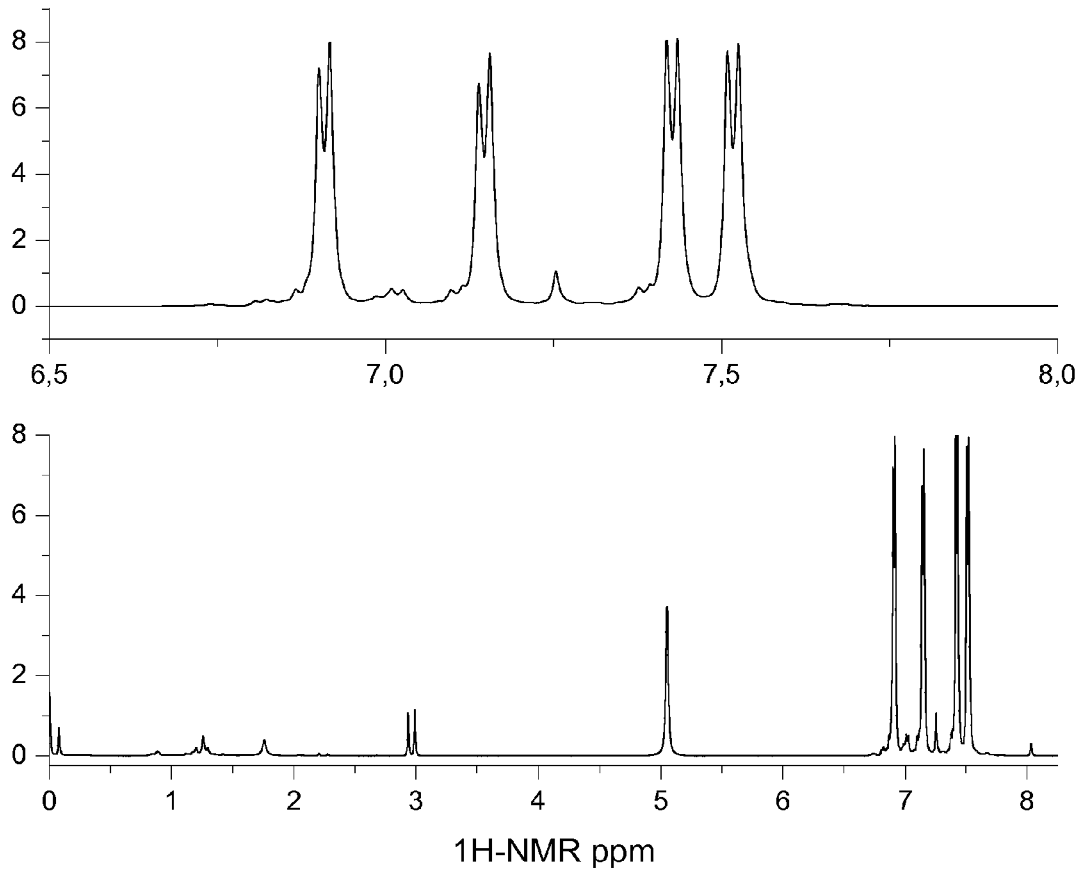
Figure 12:
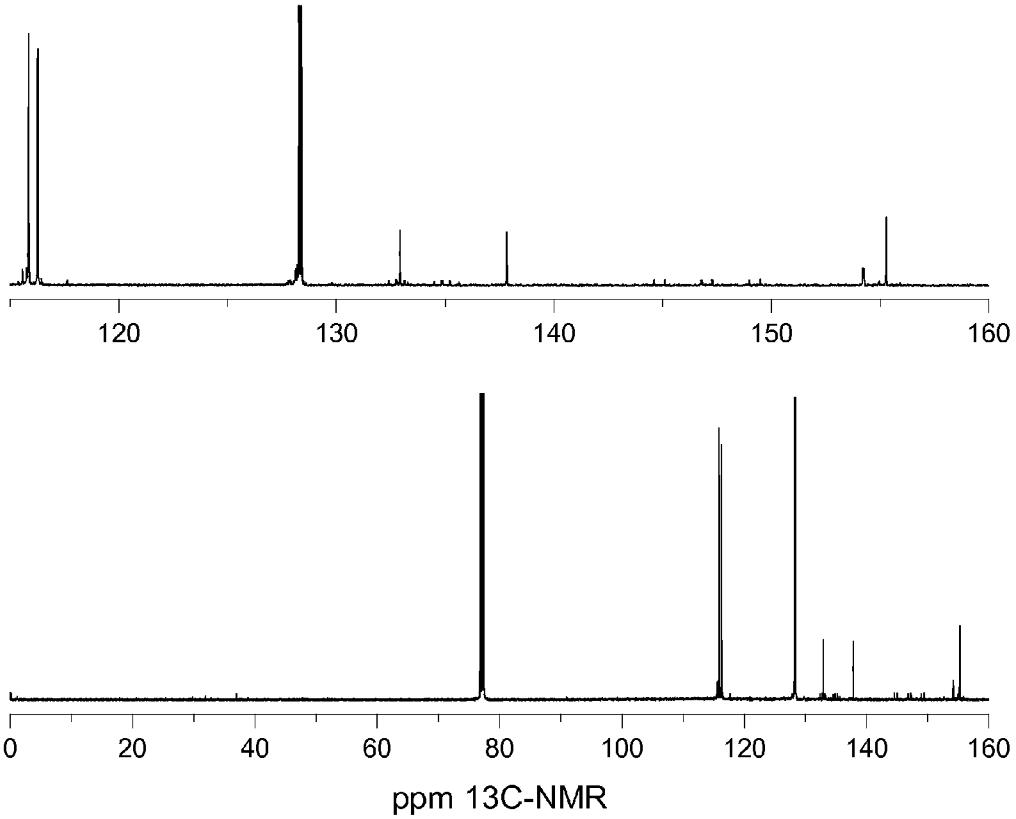

Proof of the structure was done by GC-MS, $^{19}$F-NMR (FIG. 10), 1H-NMR (FIG. 11), and $^{13}$C-NMR (FIG. 12).

Example 4

Corresponding to Route 4

Compounds with two OH-groups (e.g. bisphenol 15) can be esterified with compound 6 in equimolar amounts. The remaining OH-group can be cyanated using cyanogen-bromide. For the case of directly linked phenols, the reactivity of the OH-groups is graduated, i.e. the reactivity of the second group is reduced, after the first is esterified. This should result in the first step in the formation of a monoester (16), which can be converted into the hybrid monomer (17) using cyanogen bromide.

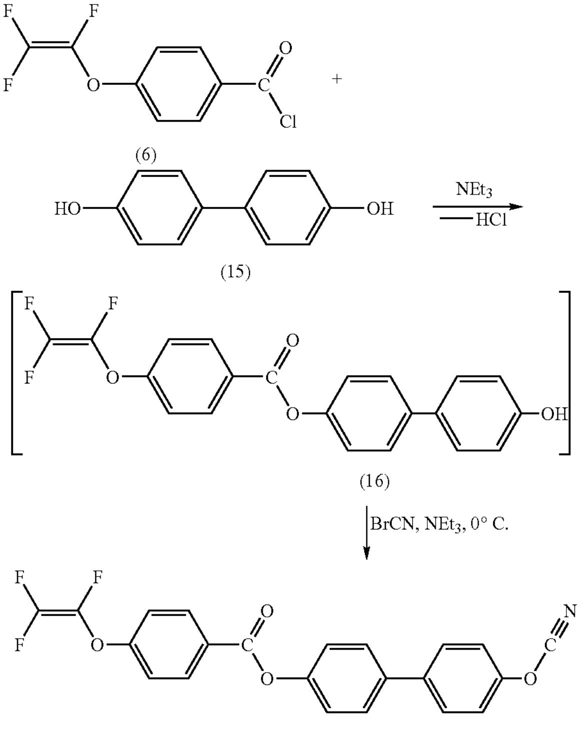

(6)

(15)

(16)

(17)

10 mmol (1.862 g) of 4,4'-bisphenole (15) were dissolved in 40 ml of dry acetone. The solution was cooled down in a three neck flask with nitrogen inlet and dropping funnel. During cooling down the solution opacified. 10 mmol (1.053 g) cyanogen bromide were added to the solution. 10 mmol (1.396 ml) of dry $NEt_3$ were dissolved into 1.5 ml of dry acetone and added dropwise within 2 min, keeping the temperature of the reaction mixture between 1 and 6° C. The mixture was stirred 20 further min. to reach 1° C. 10 mmol (1.396 ml) of dry $NEt_3$ were dissolved in 1.5 ml of dry acetone and added rapidly to the reaction mixture. 11 mmol (1.837 ml) of the TFVE-acid chloride 6 were added dropwise during 6 min. keeping the temperature in the flask between 1 and 4°

C. The mixture was allowed to stir further 30 min. IR-spectroscopy of the crude solution shows both, the ester-band and the cyanate band.

The solid (insoluble) residue was removed via filtration. The residue was washed twice with water and ethanol to remove the triethylaminohydrochloride and the triethylaminohydrobromide. The resulting white solid (1.767 g) contains only the TFVE-diester of the diphenole (IR-spectroscopy).

The workup of the reaction solution was done as follows: The acetone was removed in vacuum and a white solid was obtained, which was dissolved in chloroform, washed three times with water. The organic phase was dried over $Na_2SO_4$. The solvent was removed in vacuum and 2.49 g of a slightly yellow powder were obtained.

The product contains two main products, as may be seen from HPLC. The products can be separated using RP18-silica-gel column.

The IR-spectra of the isolated first product shows a cyanate band, but no ester band. The IR-spectra of the isolated second product shows the cyanate band and the ester band, giving proof that the second product is the desired hybrid-like monomer 17.

Example 5

Corresponding to Route 5

The synthesis of a TVE-polycyanurate-prepolymer described above in route 5 is done via a two step synthesis.

Step 1: Synthesis of the OH-Containing Cyanurate-Prepolymer (Illustrated in FIG. 2):

In the first step, 12.939 g (33.5 mmol) of 2,2'-Bis(4-cyanatophenyl)hexafluoroisopropylene (F10), 1.081 g (4.1 mmol) of 2,2,3,3,4,4,5,5-octafluorohexane-1,6-diol and 8,664 g (24.7 mmol) of 2,2,3,3,4,4,5,5,6,6,7,7,7-Tridecafluoroheptan-1-ol were heated in a sealed vial under nitrogen for three hours at 180° C. while stirring using a teflon coated magnetic stirring bar. A slightly yellow, soluble and meltable solid OH-containing prepolymer is obtained. The cyanato groups are completely converted into triazine-rings, as proven via IR-spectroscopy.

Step 2: Esterification of the OH-Containing Cyanurate-Prepolymer with TFVE-Acid chloride (Illustrated in FIG. 1):

22.684 g (33 mmol —OH) of the OH-containing cyanurate-prepolymer obtained in step 1 were dissolved in 140 ml of abs. chloroform. 6.28 ml triethylamine were dissolved in 16 ml dry chloroform. Both solutions were cooled down in a four-neck flask under nitrogen. 11.685 g (49.5 mmol) of the TVE-acid chloride were dissolved in 12 ml of dry chloroform and added dropwise to the reaction mixture during 33 min. keeping the temperature between 1 and 4° C. The mixture is allowed to react further 45 min. without cooling. The solution is extracted with water and acidified with dilute hydrochloric acid. The organic phase is washed twice with water, dried over sodium sulfate and concentrated in vacuum to an amount of approx. 70 ml. The IR-spectra of the dried solution shows that no significant amount of OH is left.

The concentrated solution is poured into 600 ml of Ethanol, resulting in the precipitation of a white solid. After filtrating and drying 16.2 g of a white powder were obtained (yield: 55.3%).

Example 6

Corresponding to Route 5

The synthesis of the TVE-polycyanurate-prepolymer described above in route 5 is done via a two step synthesis.

Step 1: Synthesis of the OH-Containing Cyanurate-Prepolymer (See FIG. 2):

In the first step (FIG. 2) 12.939 g (33.5 mmol) of 2,2'-bis (4-cyanatophenyl)hexafluoroisopropylene (F10), 1.081 g (4.1 mmol) of 2,2,3,3,4,4,5,5-octafluorohexane-1,6-diol, 2,253 g (12,375 mmol) of 2,2,3,3,4,4-hexafluorobutal-1-ol and 4,332 g (12,375 mmol) of 2,2,3,3,4,4,5,5,6,6,7,7,7-tridecafluoroheptan-1-ol were heated in a sealed vial under nitrogen for three hours at 180° C. while stirring using a teflon coated magnetic stirring bar. A slightly yellow, soluble and meltable solid OH-containing prepolymer is obtained. The cyanato groups are completely converted into triazine-rings, as proven via IR-spectroscopy.

Step 2: Esterification of the OH-Containing Cyanurate-Prepolymer with TVE-Acid chloride (See FIG. 1):

20.605 g (33 mmol —OH) of the OH-containing cyanurate-prepolymer □obtained in step 1 were dissolved in 140 ml of abs. chloroform. 6.28 ml triethylamine were dissolved in 16 ml dry chloroform. Both solutions were cooled down in a four-neck flask under nitrogen. 11.685 g (49.5 mmol) of the TVE-acid chloride (6) (see FIG. 1) were dissolved in 12 ml of dry chloroform and added dropwise to the reaction mixture during 33 min. keeping the temperature between 1 and 4° C. The mixture is allowed to react further 45 min. without cooling. The solution is extracted with water and acidified with dilute hydrochloric acid. The organic phase is washed twice with water, dried over sodium sulfate and concentrated in vacuum to an amount of approx. 70 ml. The IR-spectra of the dried solution shows that no significant amount of OH is left. The concentrated solution is poured into 600 ml of ethanol, resulting in the precipitation of a white solid. After filtrating and drying, 8.9 g of a white powder were obtained (yield: 32.7%).

Example 7

Application as Waveguide Material for Integrated Optics

Layer 1

A 55 to 65 weight-% solution of the hybrid-prepolymer described in Example 5 in 2-EEA (2-Ethoxyethylacetate) is prepared. The slightly yellow solution is filtrated under clean-room-conditions through a 0.2 μm PTFE-membrane filter using nitrogen pressure.

A thin (5-15 μm) layer is obtained by spin-coating (1.000-3.000 rpm) the solution onto a silica-substrate. To crosslink the film, the substrate is heated onto a hot-plate for 1 h at 250° C. under nitrogen. The layer-quality is very good. The refractive index (nTE) of the film is 1.4663 (measured with a Metricon prism-coupler). The optical loss of the cured layer is approx. 0.30-0.35 dB/cm @ 1550 nm. The loss measurement was done using the sliding prism method, well known to one skilled in the art.

Layer 2

A 55 to 65 weight-% solution of the Hybrid-prepolymer described in Example 5 in 2-EEA (2-Ethoxyethylacetate) is prepared. The slightly yellow solution is filtrated under clean-room-conditions through a 0.2 μm PTFE-membrane filter using nitrogen pressure.

A thin (5-15 μm) layer is obtained by spin-coating (1.000-3.000 rpm) the solution onto a silica-substrate. To crosslink the film, the substrate is heated onto a hot-plate for 1 h at 250° C. under nitrogen. The layer-quality is very good. The refractive index (nTE) of the film is 1.4740 (measured with a Metricon prism-coupler). The optical loss of the cured layer is approx. 0.35-0.40 dB/cm @ 1550 nm. The loss measurement was done using the sliding prism method, well known to one skilled in the art. Thus a refractive index-contrast of $7.7\times10^{-3}$ can be obtained using the polymer of Example 5 as a cladding layer and the polymer of Example 6 as a waveguide.

This is sufficient for a number of applications in integrated optics. Using alternate monomers, we suppose, the refractive can be adjusted in a broad range and also the optical loss can be reduced further.

What is claimed is:

1. An organic compound containing at least one trifluorovinyloxyether (TVFE) group and at least one cyanato-group, having the following formula (III):

(III)

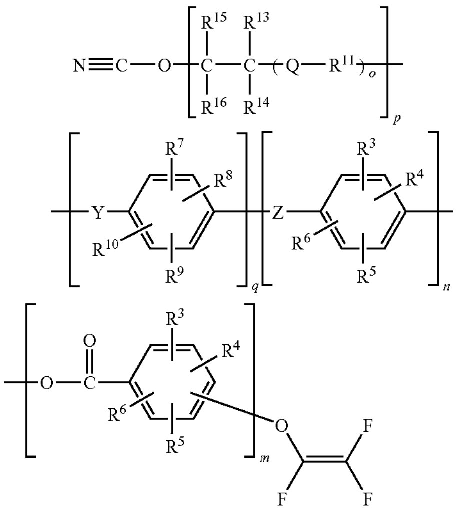

wherein the residues and indices are as follows:

$R^3$, $R^4$, $R^5$, $R^6$ are independently selected among the following groups: —H, —F, —Cl, —Br, —I, —$CH_3$, —$CF_3$, —$(CH_2)_a$—$CH_3$, —$(CF_2)_a$—CF, wherein index a is an integer, —$CH(CF_3)_2$, —$CF(CF_3)_2$, —$C(CH_3)_3$, -Ph, —$NO_2$, —$OCH_3$, —O—C(═O)—$R^{17}$, wherein $R^{17}$ is independently selected from optionally substituted alkyl groups or aryl groups, —OCN, wherein two of residues $R^3$, $R^4$, $R^5$, $R^6$ alternatively may together form a condensed aromate and alternatively or in addition, one or more of the groups $R^3$, $R^4$, $R^5$, $R^6$ can independently be selected from a cyanato group (—OCN), a trifluorovinyloxyether (TFVE) group (—O—CF═$CF_2$), residue

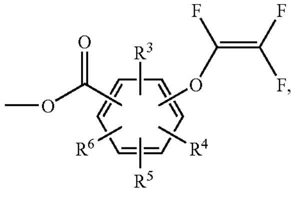

residues $R^7$, $R^8$, $R^9$, $R^{10}$ have the same meaning as defined for $R^3$, $R^4$, $R^5$, $R^6$ above, $R^{11}$ is a single bond or is an alkylene group which can be partly or fully fluorinated, $R^{13}$ and $R^{14}$ can both be F, or $R^{13}$ is F and $R^{14}$ is H, or at least one of $R^{13}$ and $R^{14}$ is an optionally partly or fully fluorinated alkyl group having 1 to 15 carbon atoms, and $R^{11}$, $R^{15}$ and $R^{16}$ can be either F or H, Y and Z are independent from each other and each Y and/or Z can independently (in case q and/or n are more than 1) be selected from a chemical bond, $SO_2$, $CF_2$, $CH_2$, CHF, $CH(CH_3)_2$, isopropylene, hexafluoroisopropylene, n- or iso-$C_1$-$C_{18}$ alkylene which may be partly or fully fluorinated, O, $NR^{19}$, N═N, CH═CH, —(C═O)—O—, —O—(C═O)—, CH═N, —C≡C—, CHN—N═CH, alkyloxyalkylene having 1 to 18 carbon atoms which is optionally partly or fully fluorinated, S, $Si(CH_3)_2$ or

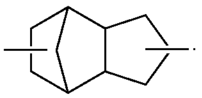

wherein $R^{19}$ is hydrogen or $C_1$-$C_{18}$ alkyl,

Q has the same meaning as Y, m is 0 or 1, n is 0, or an integer between 1 and 6, o is 0 or an integer between 1 and 12, p is 0 or 1, and q is 0 or an integer between 1 and 6.

2. The organic compound according to claim 1, containing only one trifluorovinyloxyether (TVFE) group and only one cyanato-group.

3. The organic compound according to claim 1, having the following structure (IV):

(IV)

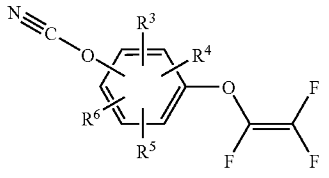

wherein the residues are as defined in formula (III) of claim 1.

4. The organic compound according to claim 1, having the following structure (V):

(V)

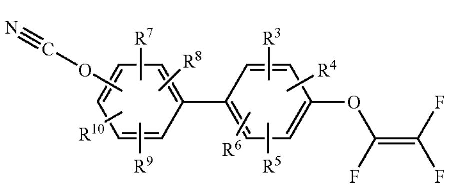

wherein the residues are as defined in formula (III) of claim 1.

5. The organic compound according to claim 1, having the following structure (VI):

(VI)

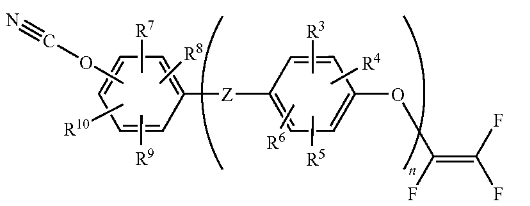

wherein the residues are as defined in formula (III) of claim 1.

6. The organic compound as claimed in claim 1 having the following structure (IX):

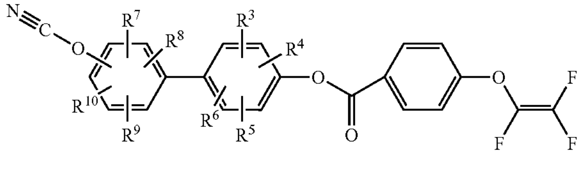

wherein the residues are as defined in formula (III) of claim 1.

7. The organic compound as claimed in claim 1, having the following structure (VII):

(VII)

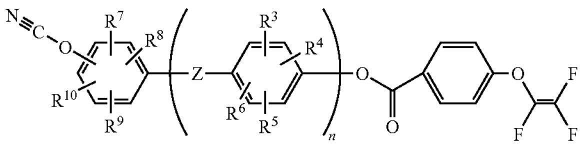

wherein the residues are as defined in formula (III) of claim 1.

8. The organic compound as claimed in claim 1, having the following structure (VIII):

(VIII)

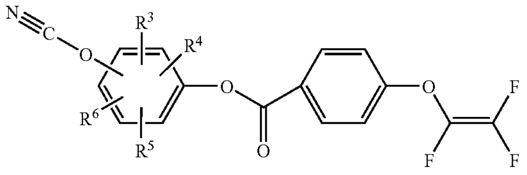

wherein the residues are as defined in formula (III) of claim 1.

9. The organic compound as claimed in claim 1, having the following structure (X):

(X)

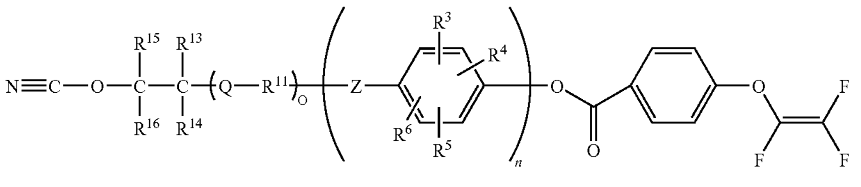

wherein the residues are as defined in formula (III) of claim 1.

10. A Method for the preparation of a compound having formula (III) as claimed in claim 1, wherein p is zero, comprising the following steps:

providing a compound having formula (XIa),

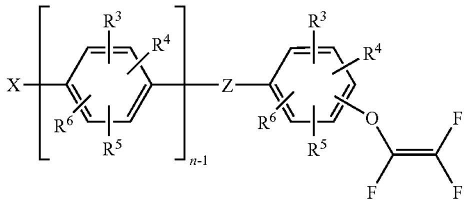

wherein the residues are as defined in formula (III) of claim 1, providing a compound having formula (XIII)

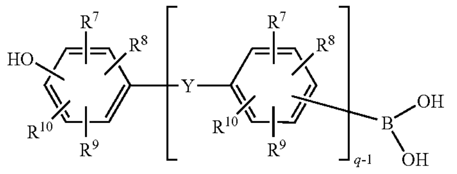

wherein the residues are as defined in formula (III) of claim 1, and coupling said compounds via Suzuki coupling, using a transition metal catalyst and basic conditions, and converting said at least one hydroxy group of the product obtained by the Suzuki coupling into a cyanato group, using a cyanogen halide, selected from cyanogen bromide and cyanogen chloride, in the presence of a Lewis base.

11. The method according to claim 10 for the preparation of a compound having the following structure (V):

(V)

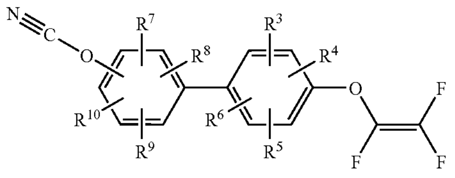

wherein the residues are $R^3$, $R^4$, $R^5$, $R^6$ are independently selected among the following groups: —H, —F, —Cl, —Br, —I, —$CH_3$, —$CF_3$, —$(CH_2)_a$—$CH_3$, —$(CF_2)_a$—CF, wherein index a is an integer, —$CH(CF_3)_2$, —$CF(CF_3)_2$, —$C(CH_3)_3$, -Ph, —$NO_2$, —$OCH_3$, —O—C(=O)—$R^{17}$, wherein $R^{17}$ is independently selected from optionally substituted alkyl groups or aryl groups, —OCN, wherein two of residues $R^3$, $R^4$, $R^5$, $R^6$ alternatively may together form a condensed aromate and alternatively or in addition, one or more of the groups $R^3$, $R^4$, $R^5$, $R^6$ can independently be selected from a cyanato group (—OCN), a trifluorovinyloxyether (TFVE) group (—O—CF═CF$_2$), residue

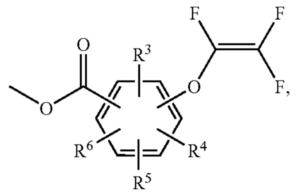

residues $R^7$, $R^8$, $R^9$, $R^{10}$ have the same meaning as defined for $R^3$, $R^4$, $R^5$, $R^6$ above, and wherein in the compound of formula (XIa), n is 0, and wherein in the starting compound of formula (XIII), q is 0.

12. The method according to claim 10, wherein in the formula (III) either q is 1 or a higher integer, or n is a or a higher integer, or q and n are independently selected from 1 or a higher integer, wherein a compound of formula (XIII) is used wherein q is 1 or a higher integer, and a compound of formula (XIa) is used wherein n is 1 or a higher integer.

13. The method for the preparation of a compound having formula (III) as claimed in claim 1, p is zero, comprising the following steps:

providing a compound having formula (XIb),

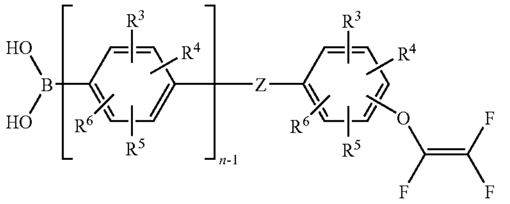

wherein the residues are as defined in formula (III) of claim 1, providing a compound having formula (XIV)

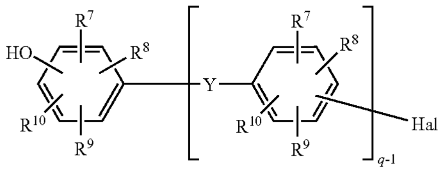

wherein the residues are as defined in formula (III) of claim 1, coupling said compounds via Suzuki coupling, using a transition metal catalyst and basic conditions, and converting said at least one hydroxy group of the product obtained by the Suzuki coupling into a cyanato group, using a cyanogen halide, selected from cyanogen bromide and cyanogen chloride, in the presence of a Lewis base.

14. The method according to claim 13 for the preparation of a compound having the following structure (V):

(V)

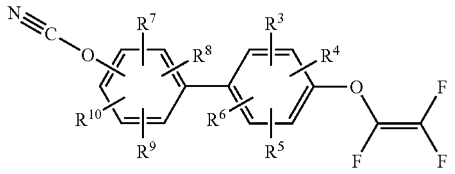

wherein the residues are $R^3$, $R^4$, $R^5$, $R^6$ are independently selected among the following groups: —H, —F, —Cl, —Br, —I, —$CH_3$, —$CF_3$, —$(CH_2)_a$—$CH_3$, —$(CF_2)_a$—CF, wherein index a is an integer, —$CH(CF_3)_2$, —CF$(CF_3)_2$, —$C(CH_3)_3$, -Ph, —$NO_2$, —$OCH_3$, —O—C(═O)—$R^{17}$, wherein $R^{17}$ is independently selected from optionally substituted alkyl groups or aryl groups, —OCN, wherein two of residues $R^3$, $R^4$, $R^5$, $R^6$ alternatively may together form a condensed aromate and alternatively or in addition, one or more of the groups $R^3$, $R^4$, $R^5$, $R^6$ can independently be selected from a cyanato group (—OCN), a trifluorovinyloxyether (TFVE) group (—O—CF═CF$_2$), residue

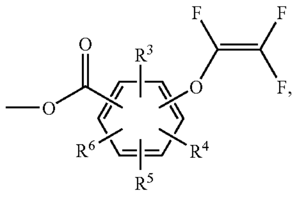

residues $R^7$, $R^8$, $R^9$, $R^{10}$ have the same meaning as defined for $R^3$, $R^4$, $R^5$, $R^6$ above, and wherein in the compound of formula (XIb), n is 0, and wherein in the starting compound of formula (XIV), q is 0.

15. The method according to claim 13, wherein in the formula (III) either q is 1 or a higher integer, or n is a or a higher integer, or q and n are independently selected from 1 or a higher integer, wherein a compound of formula (XIV) is used wherein q is 1 or a higher integer, and a compound of formula (XIb) is used wherein n is 1 or a higher integer.

16. The method for the preparation of a compound having formula (III) as claimed in claim 1, wherein either m is 0, p is 0 and at least one Z is —OC(O)—, or wherein m is 0, q is 0, and at least one Z is —OC(O)—, comprising the following steps:

providing a compound having formula (XId):

(XId)

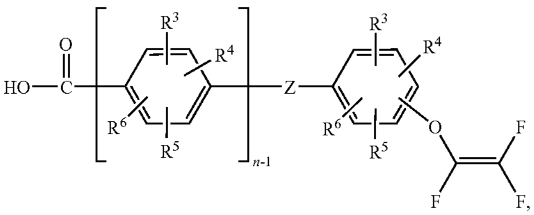

wherein the residues are as defined in formula (III) of claim 1, providing a compound having formula (XVI)

(XVI)

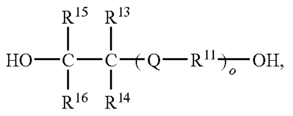

wherein the residues are as defined in formula (III) of claim 1, and reacting said compounds under conditions where esterification takes place.

17. The method according to claim 16, wherein the compounds of formula (XId) and (XV) are used in equimolar or substantial equimolar amounts.

18. The method for the preparation of a compound having formula (III) as claimed in claim 1, wherein either m is 0, p is 0 and at least one Z is —OC(O)—, or wherein m is 0, q is 0, and at least one Z is —OC(O)—, comprising the following steps:

providing a compound having formula (XId):

(XId)

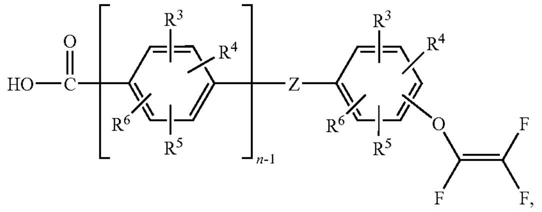

wherein the residues are as defined in formula (III) of claim 1, providing a compound having formula (XV)

(XV)

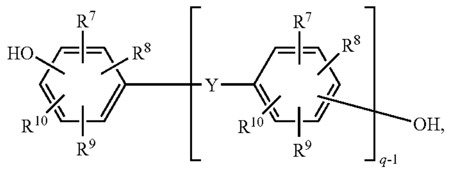

wherein the residues are as defined in formula (III) of claim 1, and reacting said compounds under conditions where esterification takes place.

19. The method according to claim 18, wherein the compounds of formula (XId) and (XV) are used in equimolar or substantial equimolar amounts.

20. Organic compound according to claim 1, wherein the residue

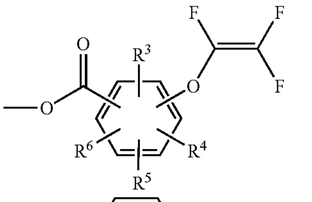

is

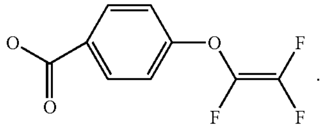

* * * * *